(12) United States Patent
Axelson, Jr. et al.

(10) Patent No.: US 9,427,334 B2
(45) Date of Patent: Aug. 30, 2016

(54) BONE PADS

(71) Applicant: Stryker Corporation, Kalamazoo, MI (US)

(72) Inventors: Stuart L. Axelson, Jr., Succasunna, NJ (US); Donald W. Malackowski, Schoolcraft, MI (US); John Michael Stuart, Rio Rancho, NM (US)

(73) Assignee: Stryker Corporation, Kalamazoo, MI (US)

( * ) Notice: Subject to any disclaimer, the term of this patent is extended or adjusted under 35 U.S.C. 154(b) by 262 days.

(21) Appl. No.: 14/195,113

(22) Filed: Mar. 3, 2014

(65) Prior Publication Data

US 2014/0257293 A1 Sep. 11, 2014

Related U.S. Application Data

(60) Provisional application No. 61/775,045, filed on Mar. 8, 2013.

(51) Int. Cl.
*A61F 2/46* (2006.01)
*A61B 17/16* (2006.01)
(Continued)

(52) U.S. Cl.
CPC ............ *A61F 2/461* (2013.01); *A61B 17/1604* (2013.01); *A61B 17/1675* (2013.01); *A61F 2/30771* (2013.01); *A61F 2/389* (2013.01); *A61F 2/3859* (2013.01); *A61B 17/1615* (2013.01); *A61F 2002/30321* (2013.01); *A61F 2002/30322* (2013.01); *A61F 2002/30807* (2013.01); *A61F 2002/30827* (2013.01); *A61F 2002/30884* (2013.01); *A61F 2002/3895* (2013.01); *A61F 2002/4631* (2013.01)

(58) Field of Classification Search
CPC .............. A61B 17/16; A61B 17/1604; A61B 17/1659; A61B 17/1662; A61B 17/1675; A61B 2017/1602; A61F 2/3859; A61F 2/389; A61F 2/46; A61F 2/4603–2/4614; A61F 2/4618; A61F 2002/4631
See application file for complete search history.

(56) References Cited

U.S. PATENT DOCUMENTS 4,055,862 A * 11/1977 Farling ................ A61F 2/38
264/122
4,550,448 A 11/1985 Kenna
(Continued)

OTHER PUBLICATIONS

Biomet, Premier Total Knee Instrumentation, 2010-2011.
(Continued)

*Primary Examiner* — Christian Sevilla
*Assistant Examiner* — Eric S Gibson
(74) *Attorney, Agent, or Firm* — Lerner, David, Littenberg, Krumholz & Mentlik, LLP

(57) ABSTRACT

Disclosed herein are systems and methods for bone preparation with designed areas having accurate tolerance profiles to enable improved initial fixation and stability for cementless implants and to improve long-term bone ingrowth/ongrowth to an implant. A method of preparing a bone surface to receive a prosthetic implant thereon having an articular surface and a bone contacting surface includes resecting the bone surface at a first location to create a first resected region having a first tolerance profile with a first cross-section, resecting the bone surface at a second location to create a second resected region having a second tolerance profile with a second cross-section less dense than the first cross-section, and contacting the bone contacting surface of the prosthetic implant with the first resected region.

19 Claims, 32 Drawing Sheets

(51) Int. Cl.
  *A61F 2/38* (2006.01)
  *A61F 2/30* (2006.01)

(56) References Cited

U.S. PATENT DOCUMENTS

| | | | |
|---|---|---|---|
| 4,919,671 A * | 4/1990 | Karpf | A61F 2/389 623/20.3 |
| 5,092,895 A * | 3/1992 | Albrektsson | A61F 2/3868 623/20.3 |
| 5,207,680 A | 5/1993 | Dietz et al. | |
| 5,344,423 A * | 9/1994 | Dietz | A61B 17/1764 606/86 R |
| 5,474,559 A * | 12/1995 | Bertin | A61B 17/154 606/86 R |
| 5,486,180 A | 1/1996 | Dietz et al. | |
| 5,560,096 A * | 10/1996 | Stephens | A61F 2/3859 29/527.6 |
| 5,593,411 A | 1/1997 | Stalcup et al. | |
| 5,601,563 A | 2/1997 | Burke et al. | |
| 5,634,927 A * | 6/1997 | Houston | A61B 17/1735 606/79 |
| 5,768,134 A * | 6/1998 | Swaelens | A61C 13/0004 433/201.1 |
| 5,853,415 A | 12/1998 | Bertin et al. | |
| 6,102,954 A * | 8/2000 | Albrektsson | A61B 17/8605 623/20.32 |
| 6,217,617 B1 * | 4/2001 | Bonutti | A61B 17/8802 623/20.14 |
| 6,676,669 B2 | 1/2004 | Charles et al. | |
| 6,702,805 B1 | 3/2004 | Stuart | |
| 6,723,106 B1 | 4/2004 | Charles et al. | |
| 7,458,991 B2 | 12/2008 | Wang et al. | |
| 7,537,664 B2 | 5/2009 | O'Neill et al. | |
| 7,674,426 B2 | 3/2010 | Grohowski, Jr. | |
| 7,695,519 B2 * | 4/2010 | Collazo | A61F 2/389 623/20.15 |
| 7,727,239 B2 * | 6/2010 | Justin | A61B 17/1615 606/86 R |
| 7,867,236 B2 * | 1/2011 | Hodorek | A61B 17/157 606/84 |
| 7,892,243 B2 | 2/2011 | Stuart | |
| 7,896,923 B2 * | 3/2011 | Blackwell | A61F 2/30721 623/20.21 |
| 7,927,335 B2 * | 4/2011 | Deffenbaugh | A61B 17/1617 606/87 |
| 8,211,113 B2 * | 7/2012 | Brown | A61B 17/1615 606/96 |
| 8,506,645 B2 * | 8/2013 | Blaylock | A61B 17/1764 623/23.22 |
| 8,535,385 B2 * | 9/2013 | Hanssen | A61F 2/30 623/23.19 |
| 8,556,908 B2 * | 10/2013 | Nycz | A61B 17/1764 606/87 |
| 8,753,401 B2 * | 6/2014 | Dee | A61F 2/30756 623/16.11 |
| 8,764,760 B2 * | 7/2014 | Metzger | A61B 17/155 606/88 |
| 8,852,195 B2 * | 10/2014 | Justin | A61B 17/1675 606/87 |
| 8,945,222 B2 * | 2/2015 | Linares | A61F 2/30 623/17.11 |
| 9,138,259 B2 * | 9/2015 | Maxson | A61B 17/1739 |
| 2002/0022889 A1 * | 2/2002 | Chibrac | A61F 2/3603 623/18.11 |
| 2002/0107573 A1 * | 8/2002 | Steinberg | A61B 17/00234 623/17.12 |
| 2002/0183760 A1 * | 12/2002 | McGovern | A61B 17/1764 606/88 |
| 2003/0005786 A1 | 1/2003 | Stuart et al. | |
| 2003/0130665 A1 * | 7/2003 | Pinczewski | A61B 17/154 606/88 |
| 2005/0143831 A1 * | 6/2005 | Justin | A61B 17/157 623/20.17 |
| 2005/0192588 A1 * | 9/2005 | Garcia | A61B 17/155 606/88 |
| 2006/0089621 A1 * | 4/2006 | Fard | A61B 17/1615 606/1 |
| 2006/0095135 A1 * | 5/2006 | Kovacevic | A61F 2/389 623/20.32 |
| 2006/0147332 A1 | 7/2006 | Jones et al. | |
| 2006/0228247 A1 | 10/2006 | Grohowski | |
| 2006/0276796 A1 * | 12/2006 | Creger | A61B 17/1767 606/79 |
| 2007/0005142 A1 * | 1/2007 | Rhodes | A61F 2/389 623/20.32 |
| 2007/0100462 A1 * | 5/2007 | Lang | A61F 2/30942 623/20.29 |
| 2007/0299532 A1 * | 12/2007 | Rhodes | A61F 2/389 623/20.32 |
| 2008/0154270 A1 * | 6/2008 | Haines | A61B 17/155 606/88 |
| 2008/0202274 A1 | 8/2008 | Stuart | |
| 2008/0234683 A1 * | 9/2008 | May | A61B 17/17 606/87 |
| 2008/0275452 A1 * | 11/2008 | Lang | A61B 17/15 606/88 |
| 2009/0076605 A1 * | 3/2009 | Linares | A61F 2/32 623/14.12 |
| 2009/0198340 A1 * | 8/2009 | Cloutier | A61B 17/1764 623/20.35 |
| 2009/0280179 A1 | 11/2009 | Neumann et al. | |
| 2009/0287222 A1 * | 11/2009 | Lee | A61B 17/1615 606/130 |
| 2009/0318584 A1 | 12/2009 | Speitling et al. | |
| 2010/0076441 A1 * | 3/2010 | May | A61B 17/1675 606/79 |
| 2010/0082034 A1 * | 4/2010 | Remia | A61B 17/8685 606/88 |
| 2010/0121459 A1 | 5/2010 | Garigapati et al. | |
| 2010/0145343 A1 * | 6/2010 | Johnson | A61B 17/025 606/85 |
| 2010/0268249 A1 | 10/2010 | Stuart | |
| 2010/0268250 A1 | 10/2010 | Stuart et al. | |
| 2010/0275718 A1 | 11/2010 | Stuart et al. | |
| 2011/0106093 A1 * | 5/2011 | Romano | A61B 17/155 606/88 |
| 2012/0330429 A1 * | 12/2012 | Axelson, Jr. | A61F 2/30771 623/20.19 |
| 2014/0012267 A1 * | 1/2014 | Sikora | A61F 2/3859 606/88 |
| 2014/0128874 A1 * | 5/2014 | Gibson | A61B 17/1746 606/79 |
| 2014/0257293 A1 * | 9/2014 | Axelson, Jr. | A61B 17/1675 606/79 |
| 2014/0277544 A1 * | 9/2014 | Viscogliosi | A61B 17/3472 623/20.32 |
| 2014/0277549 A1 * | 9/2014 | Ell | A61F 2/3859 623/20.35 |
| 2015/0164648 A1 * | 6/2015 | Lizak | A61F 2/3868 623/20.29 |
| 2016/0008136 A1 * | 1/2016 | Jones | A61F 2/389 623/20.17 |

OTHER PUBLICATIONS

Zimmer, Cruciate Retaining and Revision Instrumentation Surgical Technique, 2002, 2005, 2008, 2011.
Zimmer, Gender Solutions Patello-Femoral Joint (PFJ) System, 2008, 2009.

* cited by examiner

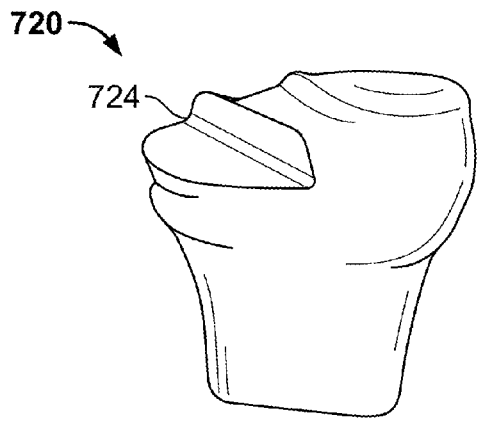
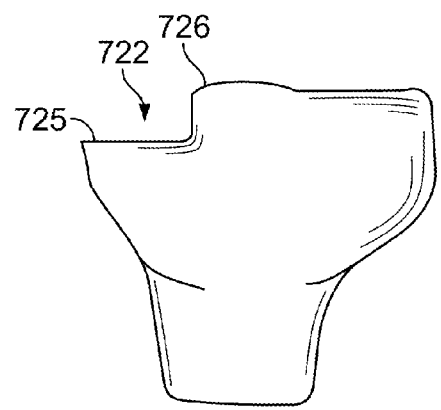
FIG. 18A    FIG. 18B
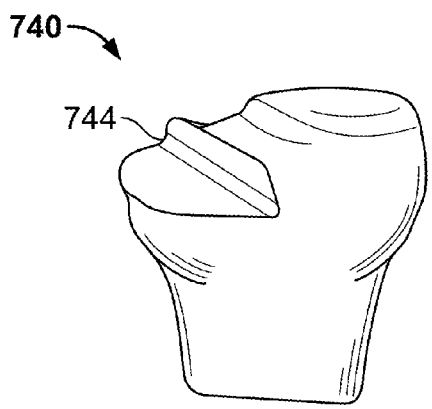
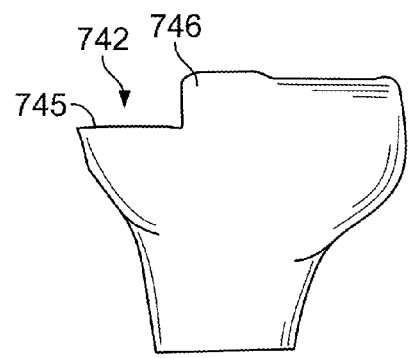
FIG. 19A    FIG. 19B
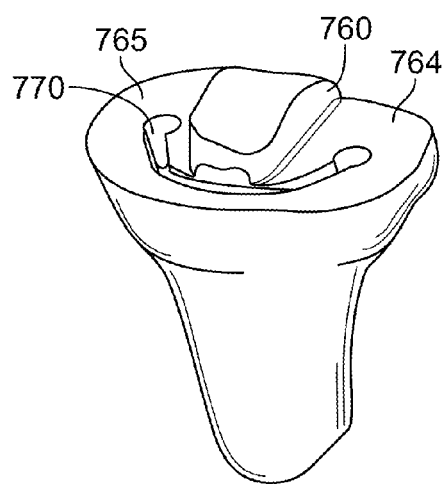
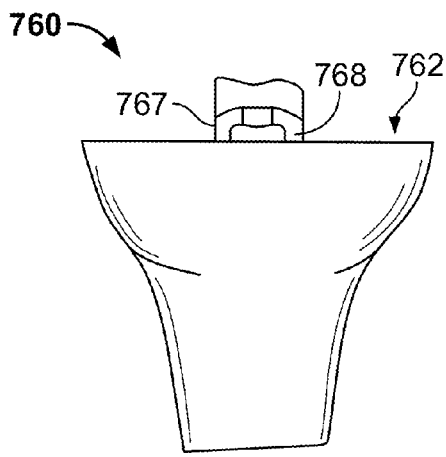
FIG. 20A    FIG. 20B

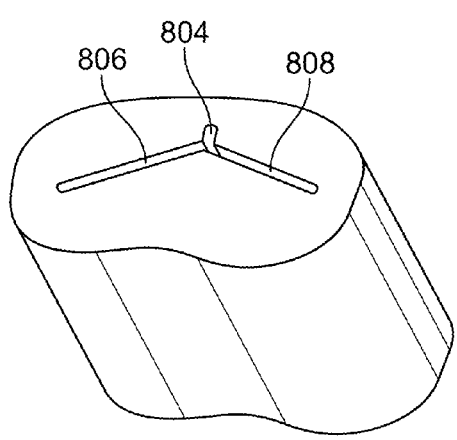
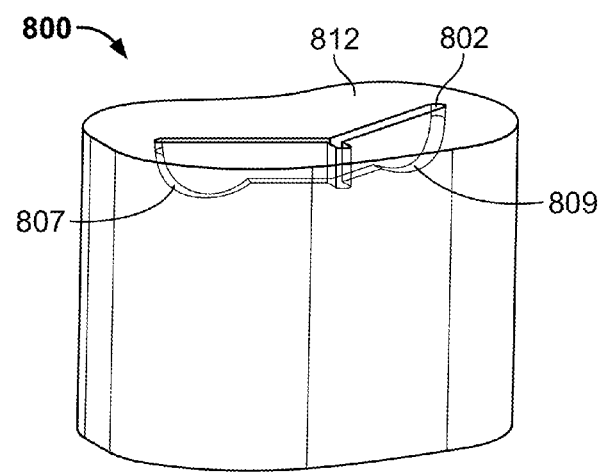
FIG. 21A       FIG. 21B
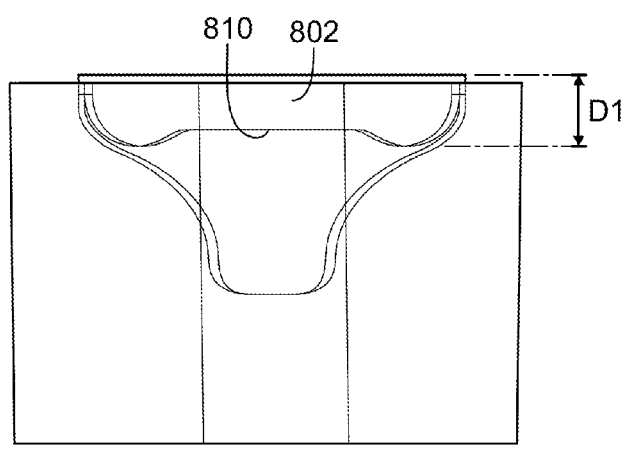
FIG. 21C

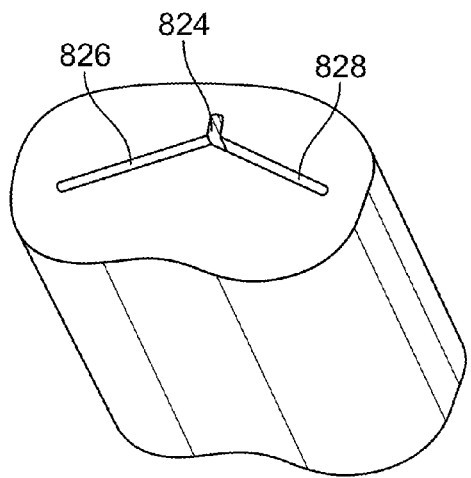
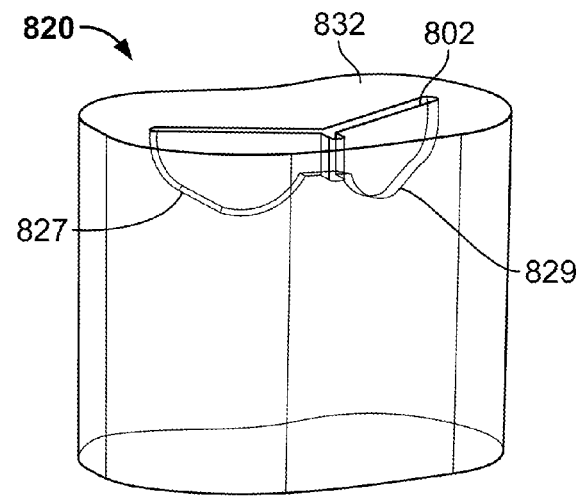
FIG. 22A    FIG. 22B
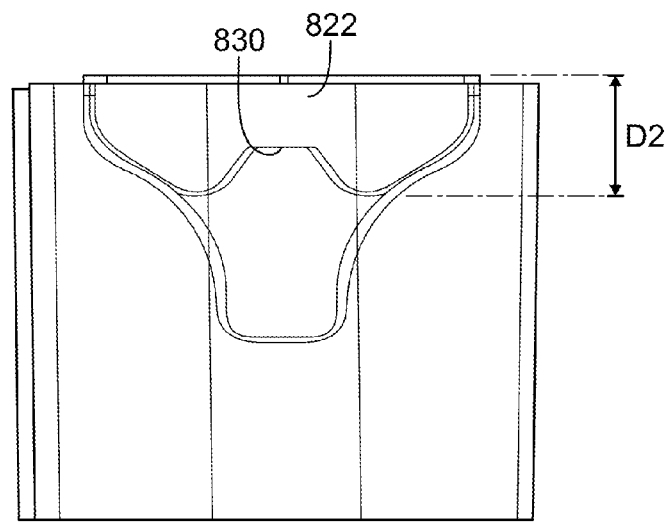
FIG. 22C

FIG. 23A  FIG. 23B

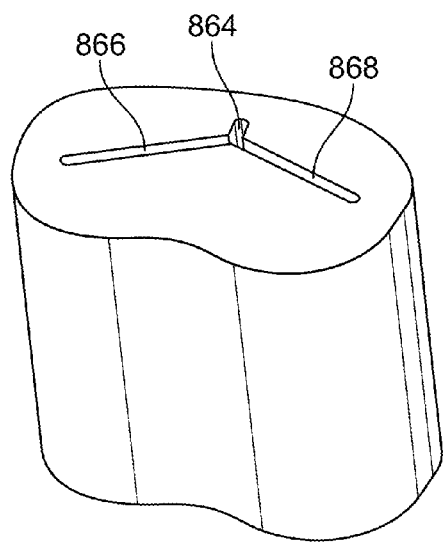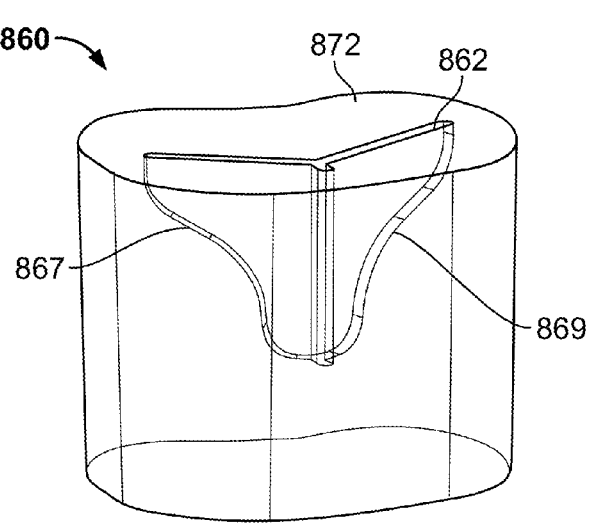
FIG. 24A  FIG. 24B
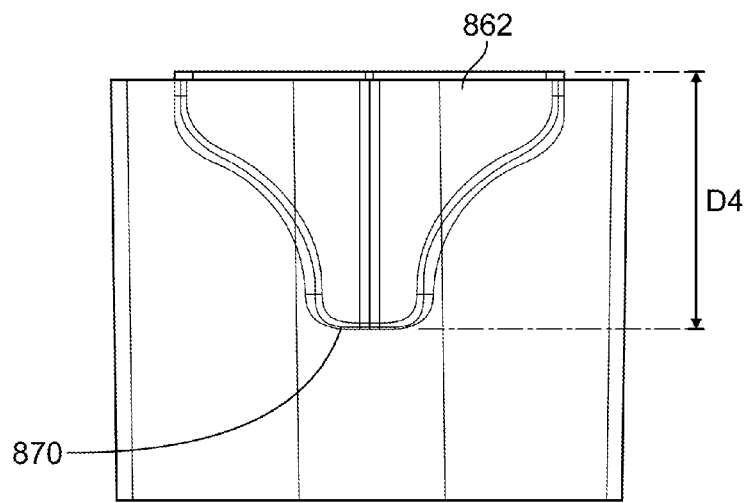
FIG. 24C

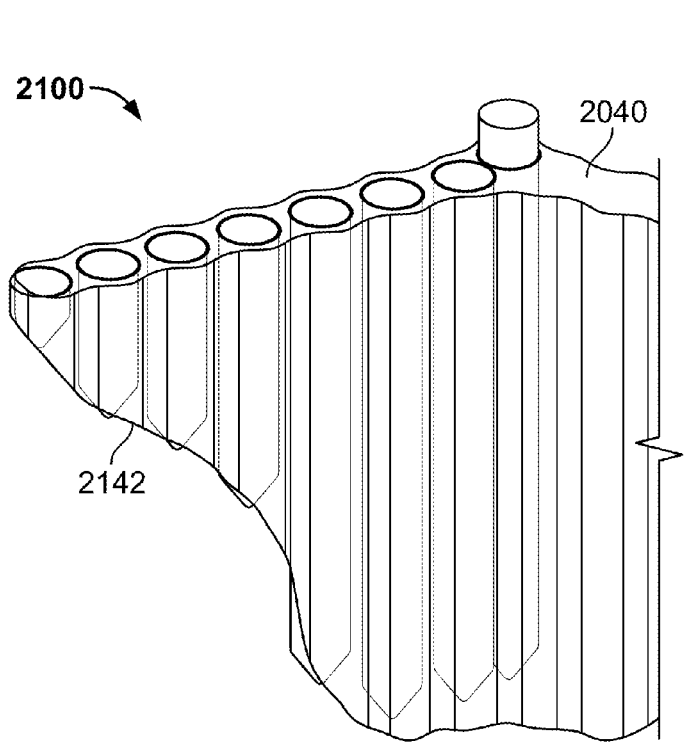
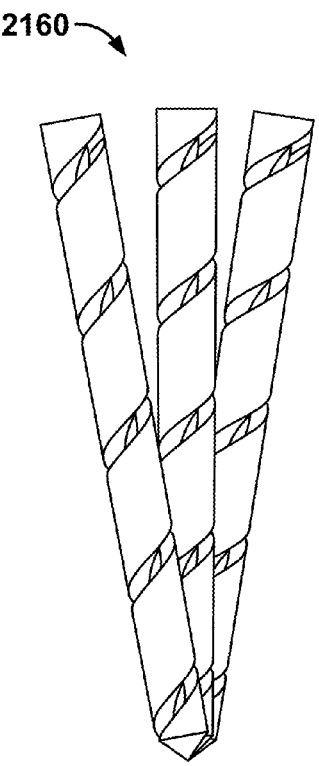
FIG. 37A  FIG. 37B
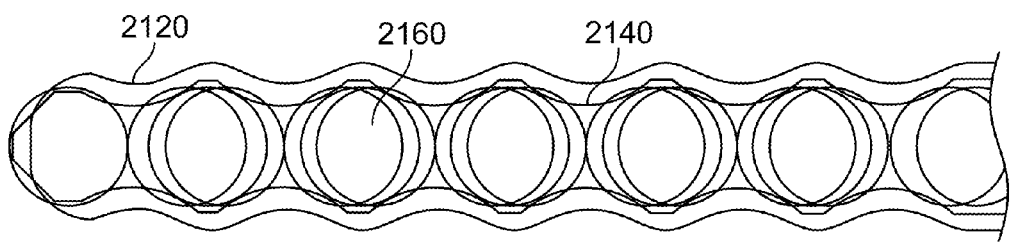
FIG. 37C
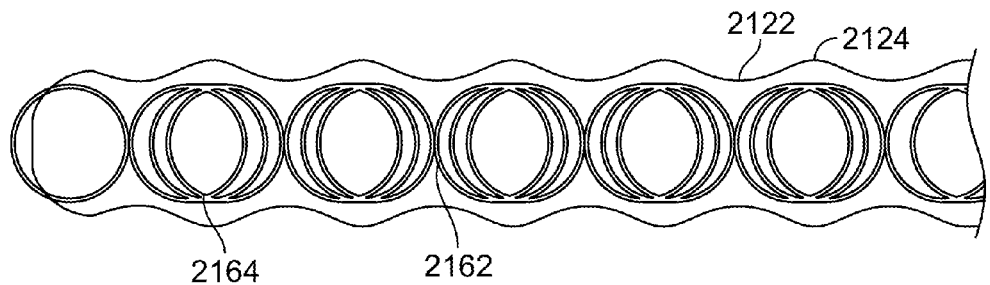
FIG. 37D

BONE PADS

CROSS-REFERENCE TO RELATED APPLICATIONS

The present application claims the benefit of the filing date of U.S. Provisional Patent Application No. 61/775,045, filed Mar. 8, 2013, the disclosure of which is hereby incorporated herein by reference.

BACKGROUND OF THE INVENTION

In a traditional knee arthroplasty surgery, the diseased bone and/or cartilage of a patient is generally removed and replaced with a prosthetic implant. A surgeon may prepare the bone using a hand-held oscillating saw blade, for instance, which generally results in a series of planar bone surface resections. Additionally, the surgeon may use a drill, broach or tamp instrument to make cylindrical holes into the bone to accommodate peg fixation features on the implant. The planar bone resections and cylindrical bone holes are generally oriented to interface with generally flat bone contacting surfaces and pegs of a prosthetic implant.

In such arthroplasty surgeries, the cartilage and/or bone of a patient may be prepared by a surgeon using conventional manual instrumentation. The instrumentation used may include, for example, planar resection guides, oscillating saws, drills, chisels, punches and reamers.

Robotic surgery may also be used in arthroplasty procedures, as well as in many different medical applications. The use of a robotically controlled bone preparation system allow for increased accuracy and repeatability of bone preparation. Rotational preparation instruments may be used during robotic surgery to prepare the bone and/or cartilage surfaces.

Bone preparation using these known methods generally provides surfaces of variable accuracy. Further, implant surfaces are generally prepared with the same level of consistency across the entire prepared bone surface. These methods of bone preparation may have a negative effect on the initial fixation of a cementless implant. If the surface does not provide a stable base for a cementless implant when initially fixed to the bone, the long term success of bone ingrowth/ongrowth onto the implant may be compromised due to micromotion, which may lead to fibrous ingrowth and subsequent bone resorption.

With advancements in robotically controlled bone preparation systems, bone preparation with specifically designed regions having increased levels of accuracy are now considered. Therefore, robotic bone preparation enables select aspects of the bone to be prepared at a generally more accurate and "tighter" tolerance compared with alternate methods of bone preparation. The degree of accuracy to which a prosthetic implant is implanted on a prepared or resected bone through robotic control depends on several factors. Among those factors include the tolerance to which the prosthetic implant is manufactured or know, the tolerance of any required tracking equipment used to position the robotic arm, and the tolerances of the robotic arm itself.

BRIEF SUMMARY OF THE INVENTION

The present invention includes bone preparation with designed areas having accurate tolerance profiles to enable improved initial fixation and stability for cementless implants and to improve long-term bone ingrowth/ongrowth to an implant. Further, the present invention includes new methods of implanting an implant onto these accurate tolerance profiles.

A first aspect of the present invention is a method of preparing a bone surface to receive a prosthetic implant thereon, the prosthetic implant having an articular surface and a bone contacting surface. The method includes resecting the bone surface at a first location to create a first resected region having a first tolerance profile with a first cross-section. The method further includes resecting the bone surface at a second location to create a second resected region having a second tolerance profile with a second cross-section, the cross-section of the first tolerance profile being denser that the cross-section of the second tolerance profile. The method further includes contacting the bone contacting surface of the prosthetic implant with the first resected region.

In one embodiment of this first aspect the method further includes forming at least one recess in the bone surface prior to implanting the prosthetic implant on the bone surface, and inserting a retention element extending from the bone contacting surface in the at least one recess in the bone surface.

In another embodiment of this first aspect the method includes applying downward force to the articular surface of the prosthetic implant to compact bone in the first resected region.

In yet another embodiment of this first aspect the method includes resecting the bone surface at a plurality of locations to create a plurality of resected regions each having a tolerance profile with a cross-section, wherein the tolerance profile of each of the plurality of resected regions is denser that the cross-section of the second tolerance profile.

In still yet another embodiment of this first aspect the first of the plurality of resected regions is preferably located at an anterior aspect of the bone. The second of the plurality of resected regions is preferably located at an outer aspect of the bone. The third of the plurality of resected regions is preferably located at a posterior aspect of the bone.

In still yet another embodiment of this first aspect the cross-section of the tolerance profile of a first of the plurality of resected regions is less dense than the cross-section of the tolerance profile of a second of the plurality of resected regions and is more dense that the cross-section of the tolerance profile of a third of the plurality of resected regions.

In still yet another embodiment of this first aspect the tolerance profile of the second resected region is preferably ±0.010 inches and the tolerance profile of the plurality of resected regions is preferably ±0.025 inches. In other embodiments, the tolerance profile of the second resected region and plurality of resected regions may be more or less than ±0.010 inches and ±0.025 inches, respectively.

BRIEF DESCRIPTION OF THE DRAWINGS

The present invention will be better understood on reading the following detailed description of non-limiting embodiments thereof, and on examining the accompanying drawings, in which:

FIG. 18A is a perspective view of one embodiment of a resected medial portion of a proximal tibia.

FIG. 18B is a front plan view of the a resected medial portion shown in FIG. 18A.

FIG. 19A is a perspective view of another embodiment of a resected medial portion of a proximal tibia.

FIG. 19B is a front plan view of the a resected medial portion shown in FIG. 19A.

FIG. 20A is a perspective view of one embodiment of a resected portion on medial and lateral sides of a proximal tibia.

FIG. 20B is a front plan view of the resected portion on medial and lateral sides of a proximal tibia shown in FIG. 20A.

FIGS. 21A-24C show varying prepared keel slot depths in the proximal tibia.

FIG. 37A is a perspective view of a punch portion of a keel punch with successive 2.5 mm drill pivot cuts following the path of an outer perimeter surface of the punch portion.

FIG. 37B is one embodiment of the angles between cuts in a 2.5 mm drill pivot cut.

FIGS. 37C-37D is an example of a transverse cross-section of the tibial prosthesis keel, the punch portion of the keel punch, and the 2.5 mm drill pivot cuts.

DETAILED DESCRIPTION

As used herein, the term "distal" means more distant from the heart and the term "proximal" means closest to the heart. The term "inferior" means toward the feet and the term "superior" means towards the head. The term "anterior" means towards the front part of the body or the face and the term "posterior" means towards the back of the body. The term "medial" means toward the midline of the body and the term "lateral" means away from the midline of the body.

Figure 1:
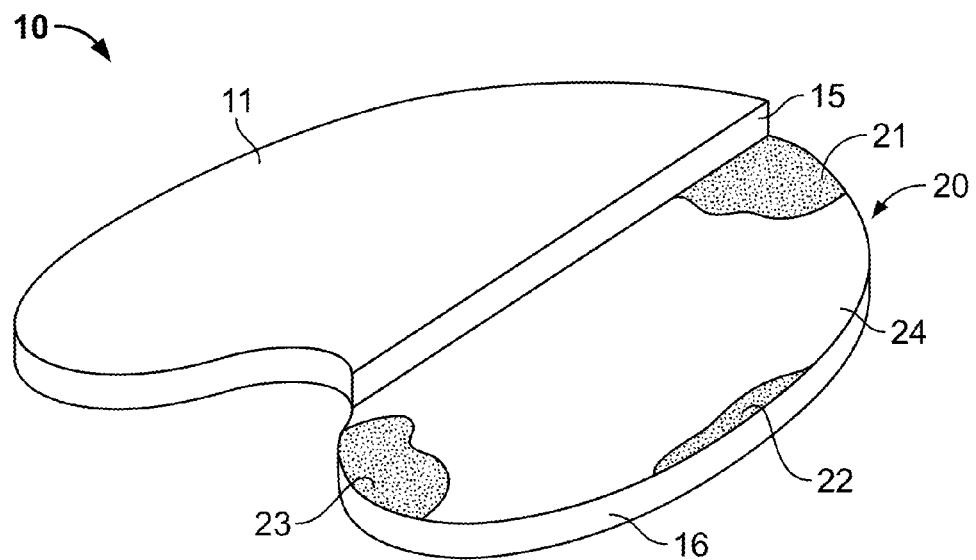
FIG. 1 is a perspective view of an embodiment of the present invention of a prepared tibial bone surface with tolerance profiles.

FIG. 1 illustrates a perspective view of a tibial bone 10. Bone 10 includes an unprepared region 11, a sagittal surface 15 and a transverse surface 20. Region 11 preferably retains unaltered or non-resected patient anatomy, which may include, for example, one or more of the following: articular cartilage, meniscus, and anterior and posterior cruciate ligament insertion regions. Sagittal surface 15 and transverse surface 20 represent cartilage/bone that have been prepared for an orthopedic procedure such as, for example, a partial knee resurfacing or unicondylar procedure. While many different types of prosthetic implants may be implanted on transverse surface 20, prosthetic implants disclosed in U.S. Ser. No. 61/500,257 titled "Prosthetic Implant and Method of Implantation" are particularly suited for implantation thereto the disclosure of which is hereby incorporated by reference herein in its entirety. In the embodiment shown, sagittal surface 15 has a generally perpendicular angular relationship to transverse surface 20. An outer bone edge 16 extends from an anterior aspect 12 of sagittal surface 15 to a posterior aspect 13 of sagittal surface 15, thus defining an outer-most edge 14 for transverse surface 20.

Figure 2:
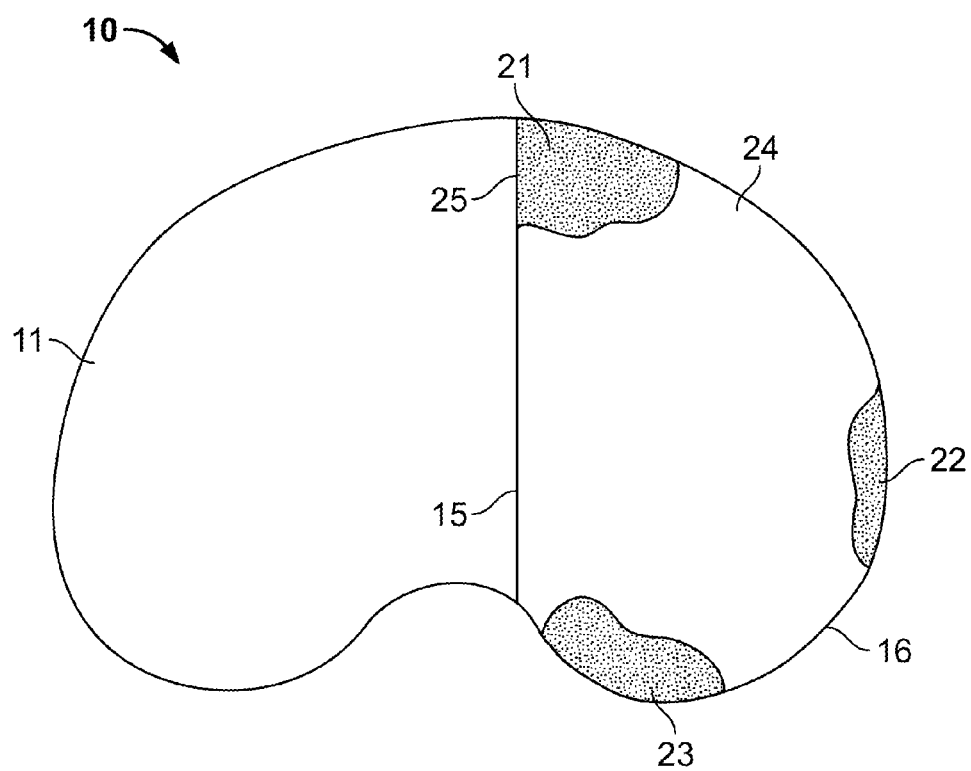
FIG. 2 is a top view of the tibial bone surface with tolerance profiles from FIG. 1.

Transverse surface 20 is comprised of an anterior zone 21, an outer zone 22, a posterior zone 23 and an internal zone 24. As shown, anterior zone 21 is adjacent to sagittal surface 15, internal zone 24 and bone edge 16. FIG. 2, which illustrates a top view of tibial bone 10, shows that anterior zone 21 has generally linear contact geometry 25 with sagittal surface 15 and non-linear contact geometries with bone edge 16 and interior zone 24. Linear contact geometry 25 approximately occupies preferably less than 33 percent of the outer profile of anterior zone 24, as shown from this top view. In other embodiments, linear contact geometry occupies between 10 and 50 percent of the outer profile of anterior zone 24, and in other embodiments occupies less than 10 and more than 50 percent of the outer profile of anterior zone 24.

As shown in FIGS. 1 and 2, both outer zone 22 and posterior zone 23 are adjacent to interior zone 24 and bone edge 16. Outer zone 22 is located along bone edge 16 between anterior zone 21 and posterior zone 23; however, the majority of the area of outer zone 22 is shifted closer toward posterior zone 23. This posterior shift of zone 22 is functionally important because the contact region between a femoral unicondylar implant and tibial unicondylar implant is generally shifted posteriorly throughout full range of leg motion. Outer zone 22 therefore may be shifted posteriorly from its position as shown in FIG. 2.

As further shown in FIG. 2, anterior zone 21, outer zone 22 and posterior zone 23 comprise approximately 40 percent of the area of transverse surface 20. Therefore, interior zone 24 comprises approximately 60 percent of the area of transverse surface 20. In other embodiments, zones 21, 22 and 23 comprise more or less that 40 percent of the area of transverse surface 20, while zone 24 comprises more or less than 60 percent of the area of transverse surface 20. Further, the respective areas of anterior zone 21 and posterior zone 23 are substantially equivalent and greater than the area of outer zone 22. In the embodiment shown, the combination of the areas of anterior zone 21 and posterior zone 23 occupy approximately 30 percent of the area of transverse surface 20.

Figure 3:
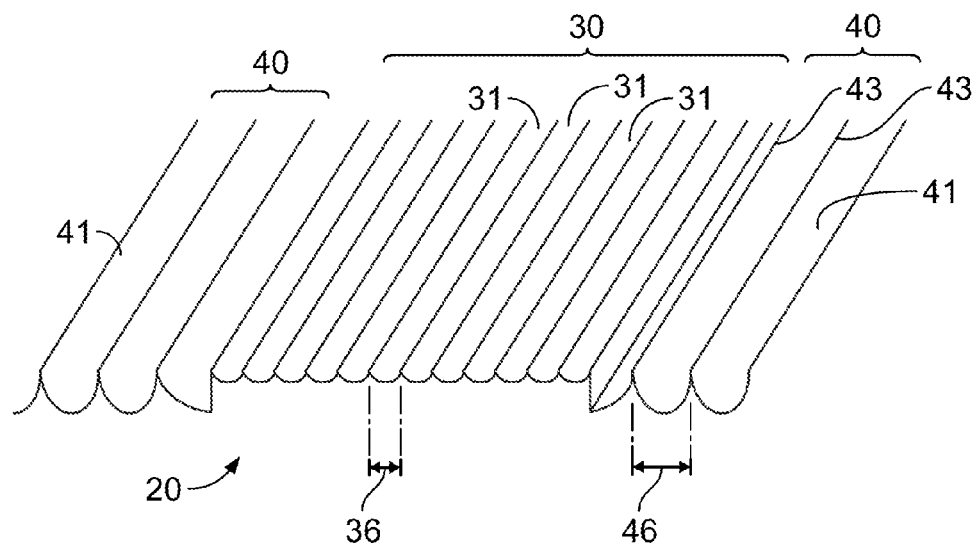
FIG. 3 is a cross-sectional perspective view of another embodiment of the present invention of a prepared bone surface with tolerance profiles.
Figure 4:
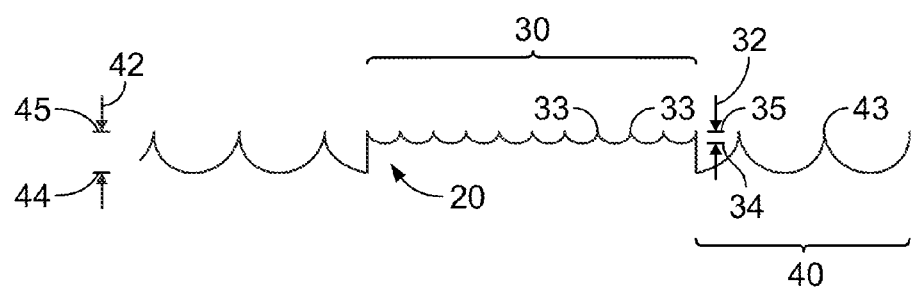
FIG. 4 is a front view of the perspective view shown in FIG. 3.

Anterior zone 21, outer zone 22 and posterior zone 23 have a substantially equivalent surface texture, which is generally represented as a tolerance profile 30 as shown in FIG. 3. The three-dimensional geometry of tolerance profile 30 is the result of a rotational cutting tool, such as a burr for example, making a plurality of channeled preparations 31 into tibial bone 10. In the embodiment shown, the plurality of channeled preparations 31 follow a substantially linear path. As shown in FIG. 4, tolerance profile 30 has a height 32, a width 36 and a plurality of protrusions 33. Height 32 is essentially the distance from the most distal bone preparation 34 made with the cutting tool to the highest relative peak 35 of the bone. In other words, height 32 may be described as the planar distance between peak 35 and trough 34 of one of the channeled preparations 31. Tolerance profile 30 is preferably designed to be very accurate, or "tight". Therefore, height 32 for all protrusions 33 are substantially consistent from protrusions 33 to adjacent protrusion 33.

Width 36 of the plurality of channel preparations 31 is defined as the distance from bone peak 35 to adjacent peak 35 in a transverse direction. Similar to the accuracy requirements for height 32, width 36 is designed to be consistent and accurate within respective zones 21, 22 and 23. Further, the tolerance profile 30, including the distal bone preparation 34 to peak 35 distance, must be substantially equivalent relative to anterior zone 21, outer zone 22 and posterior zone 23. Alternately described, the proximal-distal location relative tibial bone 30 must be accurate for respective zones 21, 22 and 23.

Interior zone 24 has a tolerance profile 40, also illustrated in FIGS. 3 and 4. The three-dimensional geometry of tolerance profile 40 is the result of a rotational cutting tool, such as a burr, making a plurality of channeled preparations 41 which follow substantially linear paths. In this embodiment, the same rotational cutting tool is used to prepare tolerance profile 30 and tolerance profile 40. Tolerance profile 40 has a height 42 as measured from the most distal bone preparation 44 to the highest relative peak 35 for a plurality of protrusions 43. In other words, height 42 may be described as the planar distance between peak 45 and trough 44 of one of the channeled preparations 41. Tolerance profile 40 also has a width 46 as measured from peak 35 to adjacent peak 35 in a transverse direction. Tolerance profile 40 is not required to be as accurate, or "tight", as the tolerance profile 30 for zones 21, 22 and 23. As show in FIGS. 3 and 4, tolerance profile 30 has a denser cross-section than that of the cross-section of tolerance profile 40.

Alternately described, height 42 and width 46 of profile 40 are larger than height 33 and width 36 of profile 30. Further, there is a lesser requirement for consistency from protrusion 43 to protrusion 43 for profile 40 that for the respective protrusion 33 to protrusion 33 consistency in profile 30. Simply stated, the preparation for interior zone 24 may be performed faster, with less rotational instrument passes across the bone, and with less accuracy than for anterior zone 21, outer zone 22 and posterior zone 23.

The cartilage and/or bone of tibial bone 10 may be prepared with the assistance of a robot. Robot assisted bone preparation may include: implant specific software, saw cutting, milling/burring or other rotational cutting instruments and various levels of surgeon interface. For example, in a first robot mode, the robot may perform the cartilage/bone preparation with the surgeon observing. In such a mode, the surgeon may not have any control over the movement of the robot or may instead be controlling the movement of the robot remotely. In a second robot mode, the surgeon may actually guide a rotational cutting tool within a predetermined boundary. In the second mode, the implant specific software is preferably programmed within the robot, which establishes boundary constraints for the preparation. Here, the surgeon will not be able to extend the preparation outside of a specific boundary. For the bone preparation shown, the surgeon preferably uses a combination of both the first and second robot modes and uses a burr as the cutting tool. In both the first and second robot modes, the surgeon would be able to stop the robotic preparation if necessary. Such robotic technology that may be applied for use with the present invention includes that described in U.S. Pat. Nos. 6,676,669, 7,892,243, 6,702,805, and 6,723,106 as well as U.S. Patent Application Nos. 2010/0268249, 2008/0202274, 2010/0268250, 2010/0275718, and 2003/0005786, the disclosures of which are all hereby incorporated by reference in their entireties.

Figure 5:
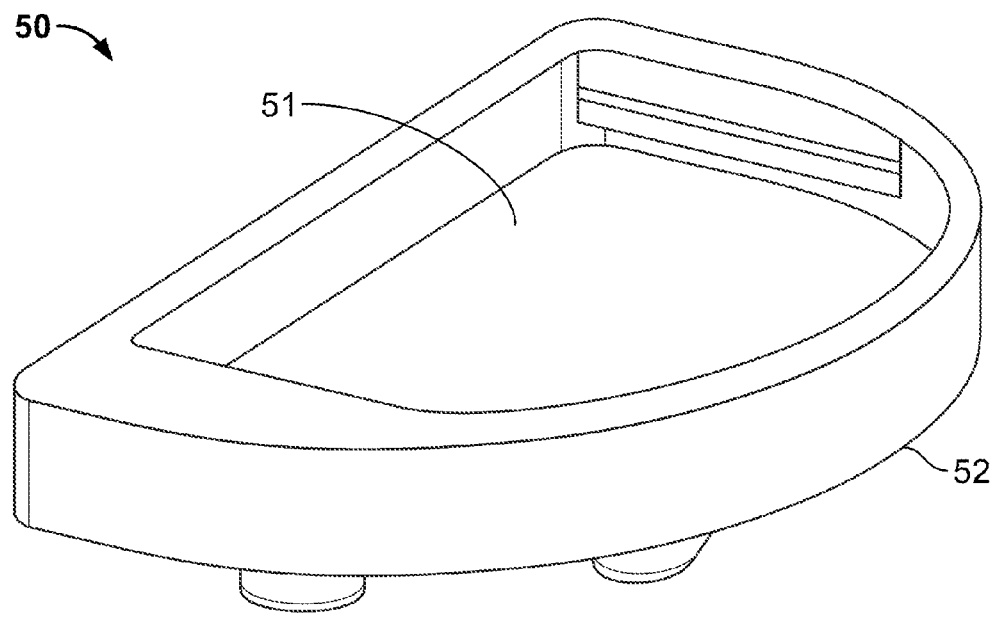
FIG. 5 is a perspective view of an embodiment of a unicondylar tibial implant.

Once the bone is prepared as previously described, the prosthetic tibial implant 50, shown in FIG. 5, may be implanted on the prepared bone surface. Implant 50 is a modular style, unicondylar design that has a proximal surface 51 and a distal surface 52. The modular style indicates that a separate polyethylene insert (not shown) is assembled to proximal surface 51. Distal surface 52 is designed for cemented or cementless fixation to the bone and includes a porous ingrowth/ongrowth structure such as beads or a porous metal structure. An example of a beaded ingrowth structure is described in U.S. Pat. No. 4,550,448, the disclosure of which is hereby incorporated by reference herein in its entirety. The porous metal structure may be manufactured from the technology described in U.S. Pat. No. 7,537,664, U.S. Patent Application No. 2006/0147332, U.S. Pat. No. 7,674,426, U.S. Patent Application No. 2006/0228247 and U.S. Pat. No. 7,458,991, the disclosures of which are all hereby incorporated by reference in their entireties.

Implant 50 is implanted onto tibial bone 10 by initially contacting peaks 35 of anterior zone 21, outer zone 22 and posterior zone 23. After implant 50 has established contact, a force is applied to proximal surface 51. The applied force results in the compaction of the plurality of protrusions 33 until the implant reaches the final seating location on distal bone preparation 34. The compaction of bone preferably has an improved biologic effect on the biologic ingrowth/ongrowth process. When implant 50 is seated in a final location, the implant is preferably contacting anterior zone 21, outer zone 22, posterior zone 23 and sagittal surface 15. Contact with respect zones 21, 22 and 23 preferably results in an accurate and stable surface for the implant 50 because of the accuracy of tolerance profile 30. In the embodiment shown, implant 50 is not in contact with interior zone 24; however, the distance between distal surface 52 and peaks 45 will be at a distance conducive to future bone ingrowth/ongrowth.

Figure 6:
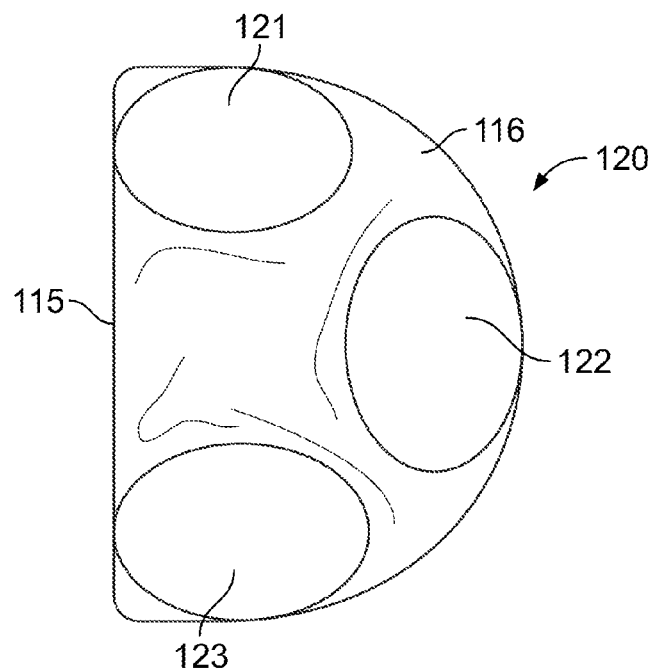
FIG. 6 is a top view of another embodiment of the present invention of a prepared tibial bone surface with tolerance profiles.

FIG. 6 shows an alternate embodiment of a prepared tibial bone 110 having a transverse surface 120 including an anterior zone 121, an outer zone 122, a posterior zone 123, an interior zone 124, a sagittal surface 115 and a bone edge 116. Both anterior zone 121 and posterior zone 123 are adjacent to sagittal surface 115, bone edge 116 and interior zone 124. While sagittal surface 115 may have a substantially perpendicular relationship with transverse surface 120, surface 115 may also have a non-perpendicular relationship with surface 120. Outer zone 122 is preferably adjacent to both interior zone 124 and bone edge 116. The geometry for zones 121, 122, 123 and 124 may be any combination of linear or non-linear geometries as previously described. It is understood that each zone may have a unique geometry, or alternatively, each zone may have zone geometries that are substantially similar, or any other combination thereof. In the embodiment shown, respective zones 121, 122 and 123 occupy approximately 50 percent of prepared transverse surface 120. Therefore, interior zone 124 also occupies approximately 50 percent of prepared transverse 120. In other embodiments, zones 121, 122 and 123 comprise more or less that 50 percent of the area of transverse surface 120, while zone 124 comprises more or less than 50 percent of the area of transverse surface 120. As shown, the percent area of coverage is substantially equivalent for zones 121, 122 and 123. Any tolerance profiles are consistent with that previously described for all zones.

In yet other embodiments, which are not shown, the range of coverage for the combination of the anterior zone, outer zone and posterior zone may range between 10 and 90 percent. In still yet other embodiments, the range or coverage for the combination of the anterior, outer and posterior zones may be less than 10 percent or more than 90 percent. Further, the range of coverage for the anterior zone, outer zone, posterior zone may be substantially similar, different, or any combination thereof. In all embodiments, the tolerance profiles are consistent with that previously described for all zones.

Figure 7:
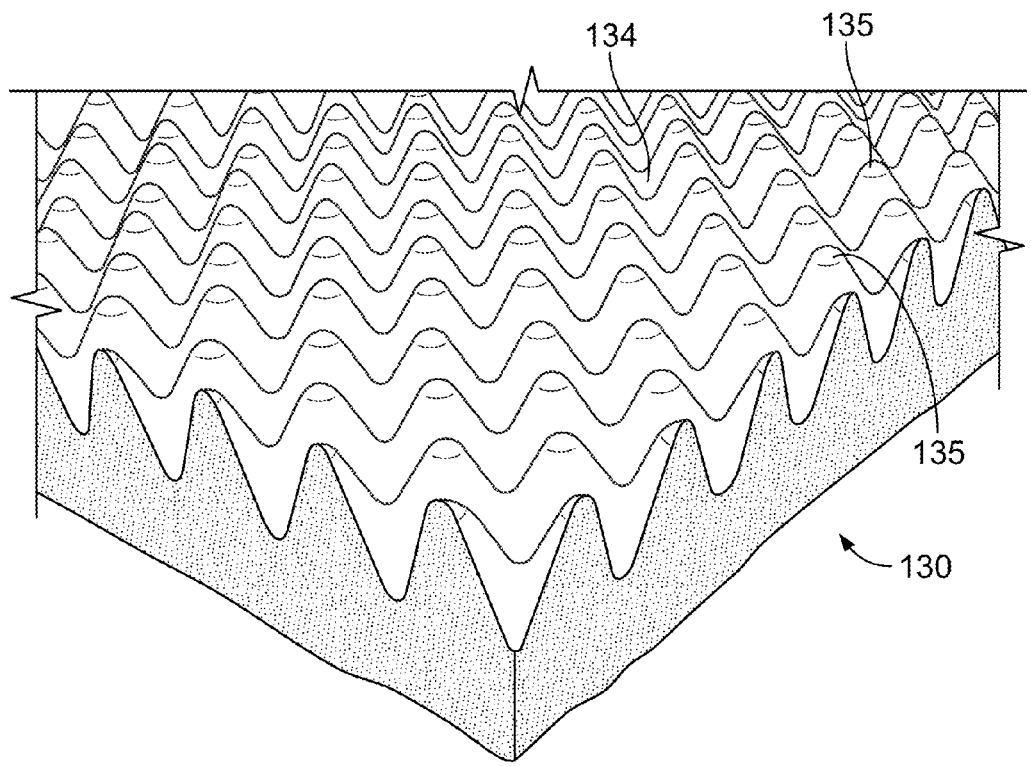
FIG. 7 is a perspective view of another embodiment of the present invention of a tolerance profile.
Figure 8:
FIG. 8 is a cross-sectional view taken along line B-B of the tolerance profiles shown in FIG. 7.

FIG. 7 shows a perspective view of an alternate embodiment of the geometry of a tolerance profile 130 that may be applied to any of the anterior, outer, posterior or interior zones previously described. Here, the three dimensional geometry of tolerance profile 130 is essentially a sinusoidal or pyramid-like pattern consisting of a plurality of peaks 135 and plurality of distal bone preparations 134. A cross-sectional side view of the preparation is illustrated in FIG. 8. Regarding FIGS. 7 and 8, the geometry may be accomplished by a series of generally linear passes of a rotational cutting instrument, followed by a series of generally orthogonal rotational cutting instrument passes. In another embodiment, the relationship between cutting instrument passes may be at a non-orthogonal angle. In yet other embodiments, the cutting path for the rotational cutting instrument may be circular, or any other non-linear path, or any combination of linear and non-linear paths.

Figure 9:
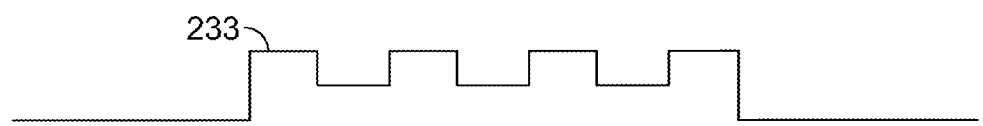
FIG. 9 is a cross-sectional view of another embodiment of the present invention of a tolerance profile.

FIG. 9 shows a cross-sectional view of another embodiment of the geometry of a tolerance profile for any of, or any combination of tolerance profiles for anterior, outer, posterior or interior zones. Here, the general shape of protrusions 233 is substantially rectangular. It is envisioned that in yet other embodiments, a rotational cutting tool may take multiple cutting paths resulting in many geometrical shapes such as circular, square, trapezoid or any other linear or non-linear geometries.

Figure 10:
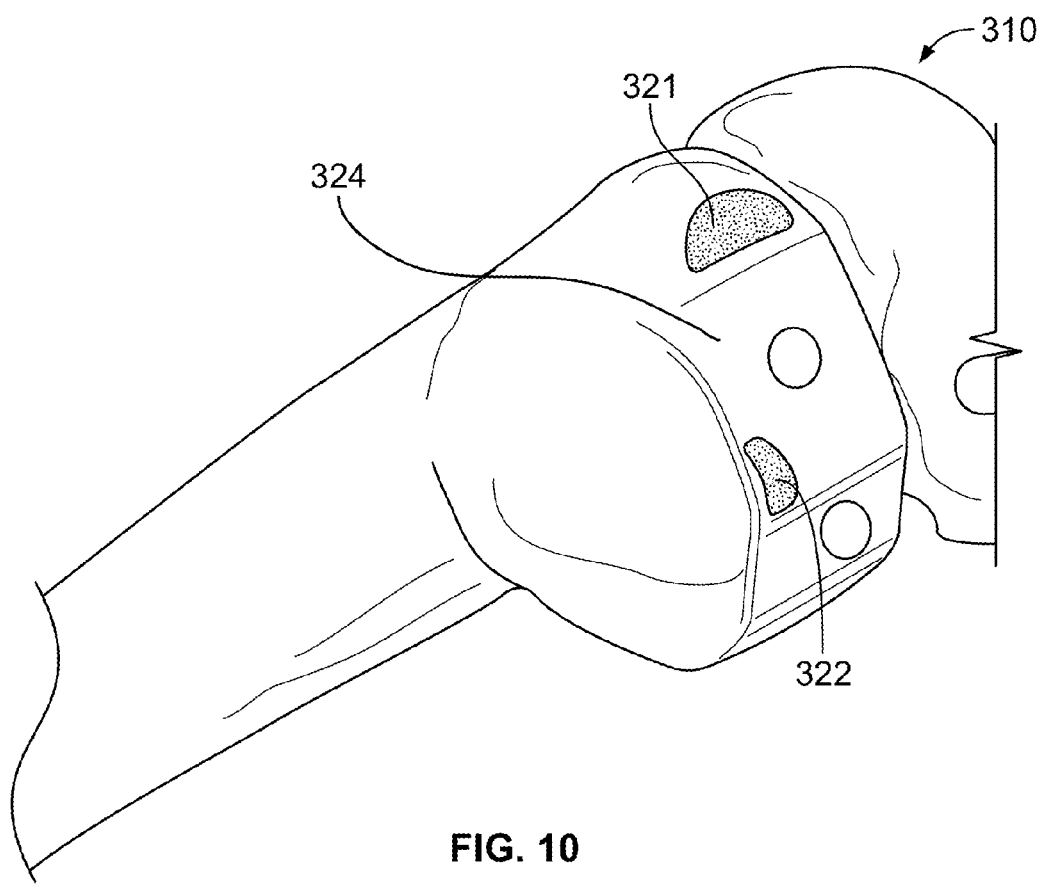
FIG. 10 is a perspective view of one embodiment of the present invention of a prepared femoral bone with tolerance profiles.
Figure 11:
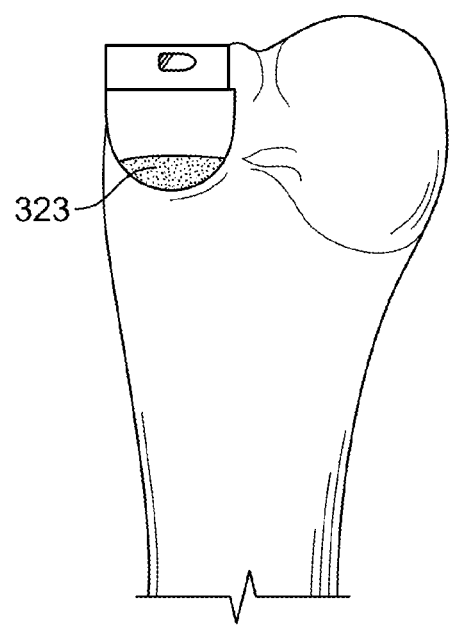
FIG. 11 is a view from a posterior aspect of the prepared femoral bone with tolerance profiles shown in FIG. 10.

FIG. 10 illustrates a view of the distal aspect of a femoral bone 310 and FIG. 11 illustrates a view of the posterior aspect of femoral bone 310. Here, femoral bone 310 has been prepared to receive a unicondylar femoral implant (not shown). Consistent with that previously described, the bone is prepared using a rotational cutting tool guided by a surgeon, robot, or combination thereof. Femoral bone 310 includes an anterior zone 321, an outer zone 322, a posterior zone 323 and an interior zone. Zones 321, 322 and 323 share a substantially similar tolerance profile 330 (not shown). Interior zone 324 has a tolerance profile 340 (not shown) which is different than profile 330. Profile 330 is designed as a more accurate and "tighter" tolerance compared with profile 340. The methods of implantation are also consistent with that previously described.

Figure 12:
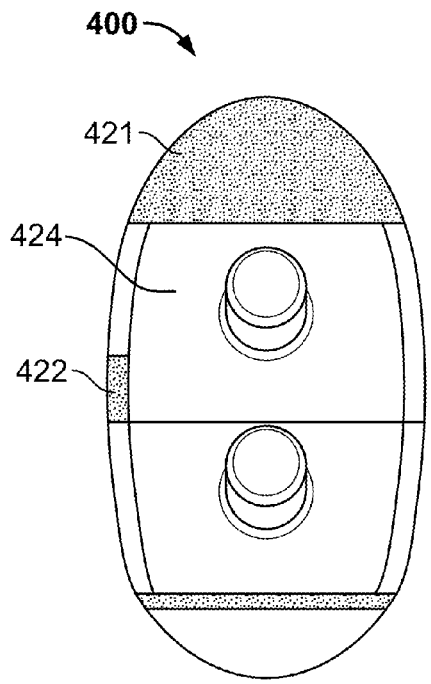
FIG. 12 is a view of a distal bone contacting surface of a unicondylar femoral implant.
Figure 13:
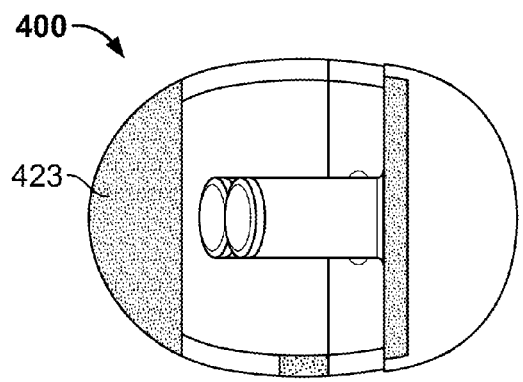
FIG. 13 is a view of a posterior bone contacting surface of the unicondylar femoral implant from FIG. 12.
Figure 14:
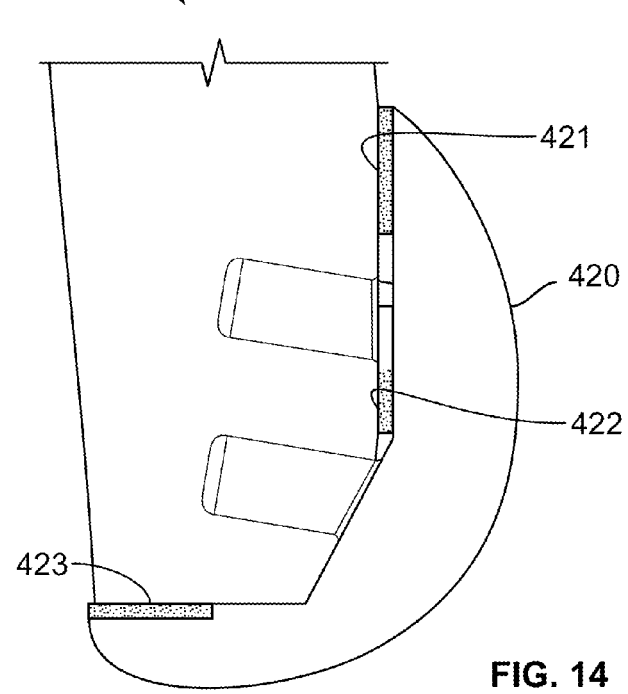
FIG. 14 is a side view of the unicondylar femoral implant of FIG. 12.

FIGS. 12-14 illustrate an embodiment of a unicondylar femoral component 400 having an articular surface 420 and a bone contacting surface 424. Here, the implant includes an anterior zone 421, an outer zone 422 and a posterior zone 423 designed to mate with the prepared femoral bone, such as previously described. Zones 421, 422 and 423 may have any geometry, or combination of geometries such as: spherical indentations, generally cylindrical indentations, sinusoidal, or other geometry. The concept is that zones 421, 422 and 423 would be manufactured with a tighter degree of tolerance as compared with other aspects of the implant. Further, the specific geometry of these respective zones is designed to improve secure initial fixation to the prepared bone surface and promote ingrowth/ongrowth.

Another aspect of the present invention is to apply a bone adhesive to the interior zone of the bone preparation or to an interior zone of an implant component. An example of a medical adhesive is described in U.S. Patent Application Nos. 2009/0318584, 2009/0280179, and 2010/0121459, the disclosures of which are hereby incorporated by reference herein in their entirety. In this aspect of the present invention, the bone adhesive would provide initial fixation to an interior zone, which is prepared to a larger tolerance profile, but will preferably resorb over time allowing for bone ingrowth/ongrowth.

Figure 15:
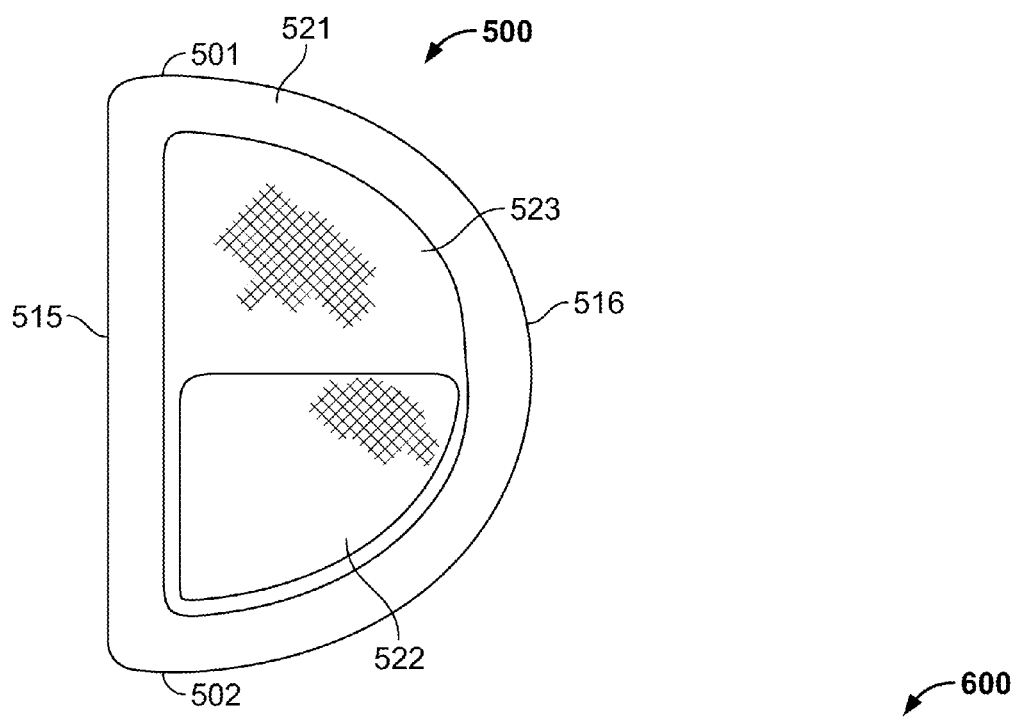
FIG. 15 is a top view of a tibial bone surface showing yet another embodiment of the present invention of tolerance profiles.

FIG. 15 shows a prepared tibial bone surface with an alternate tolerance profile pattern. Here, tibial bone has an anterior end 501, a posterior end 502, a sagittal surface 515 and an outer edge 516. The bone is prepared to three different tolerance zones: peripheral zone 521, posterior zone 522 and anterior zone 523. These three tolerance zones are each prepared to different levels of tolerance accuracy. For example, peripheral zone 521 is prepared to be the more accurate zone of the three tolerance zones. Anterior zone 523 is prepared to be the least accurate tolerance zone and has a surface area percentage less than anterior zone 523. Posterior zone 522 has an accuracy ranging between respective zones 521 and 523. As a specific example, peripheral zone 521 has a tolerance of ±0.010 in, posterior zone 522 has a tolerance of +0.010/−0.025 in, and anterior zone 523 has a tolerance of ±0.025 in.

The known anatomy of the proximal end of a tibial bone is that the periphery, or outer region, of the bone is cortical bone and the interior regions are cancellous bone. Regions of the cancellous bone may have different densities. For example, the cancellous bone in the posterior regions of the proximal tibial may be denser than bone in the anterior region of the cancellous bone. This may be the result of increased loading of this region of the proximal tibia, and via wolf's law, bone is remodeled in response to the increased loading.

Tolerance zones 521, 522 and 523 of FIG. 15 are now further described with respect to the anatomy of a proximal tibial bone 500. Peripheral zone 521 substantially covers cortical bone which extends along outer edge 516. In this embodiment, peripheral zone 521 is also substantially adjacent to sagittal surface 515. Posterior zone 522 substantially covers a region of dense cancellous bone compared to the cancellous bone covered by region 523. Zones 522 and 523 are in part adjacent to peripheral zone 521. The density of the cancellous bone of a patient by be determined preoperatively by MRI, CT, DEXA or other know scanning means. Alternately, the density of the bone may be determined interoperatively using a known scanning means, visually by the surgeon or through physical surgeon contact.

Figure 16:
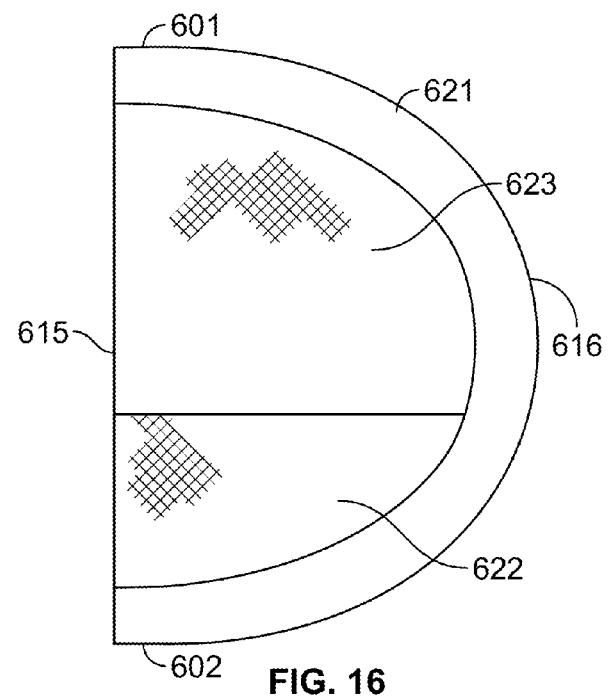
FIG. 16 is a top view of another embodiment of the present invention of a prepared tibial bone.

FIG. 16 illustrates a top view of an alternate embodiment of a prepared tibial bone 600. Bone 600 has an anterior end 601, a posterior end 602, a sagittal surface 615 and an outer edge 616. Bone 600 has three tolerance zones: a peripheral zone 621, a posterior zone 622 and an anterior zone 623. Peripheral zone 621 extends along outer edge 616 and substantially covers the cortical bone region of bone 600. Posterior zone 621 substantially covers a region of dense cancellous bone compared to the cancellous bone covered by region 623. Here, zones 622 and 623 are adjacent to sagittal surface 515.

In alternate embodiments of tibial bone 500 and bone 600, any of the previously describe combinations of limitations may be utilized. For example, the relationship of surface area coverage may vary between tolerance zones. Also, the accuracy of tolerance preparation may range from ±0.001 to ±0.100, and include any combination of tolerances therein. In yet alternate embodiments, posterior zone 522 or 622, may substantially cover an area of dense cancellous bone and be substantially surrounded by a less accurate tolerance zone, 523 or 623 respectively.

In all embodiments described above, there was an anterior zone, outer zone and posterior zone which are held to a more accurate, or "tighter," tolerance than an interior zone. In alternate embodiments, there may be less than three zones held to a more accurate tolerance profile. In yet other embodiments, there may be more than three zones held to a more accurate tolerance profile.

Conventional instruments used in orthopaedic surgeries often include the use of sawblades, punches, and chisels that have many limitations. For example, surgeons often overprepare or leave sharp corners in bone using these conventional instruments as a result of the dimensions thereof. Further, the geometry of the resected bone using these conventional instruments is generally the result of the skill and accuracy of the surgery.

The following embodiments that will be described herein use a burr tool having a certain diameter and robotic technology to prepare bone with more accuracy and control. Surgeons using these tools will no longer be limited to making planar resections with standard alignment instrumentation or punches and chisels to remove bone. By using a burr tool, the robot can prepare bone to any preoperatively planned shape or intraoperatively desired shape based on the capabilities of the robot. For example, the burr tool can be used to cut radiused edges to a desired tolerance, as opposed to sharp corners that generally result from surgeries using conventional instrumentation.

Figure 17:
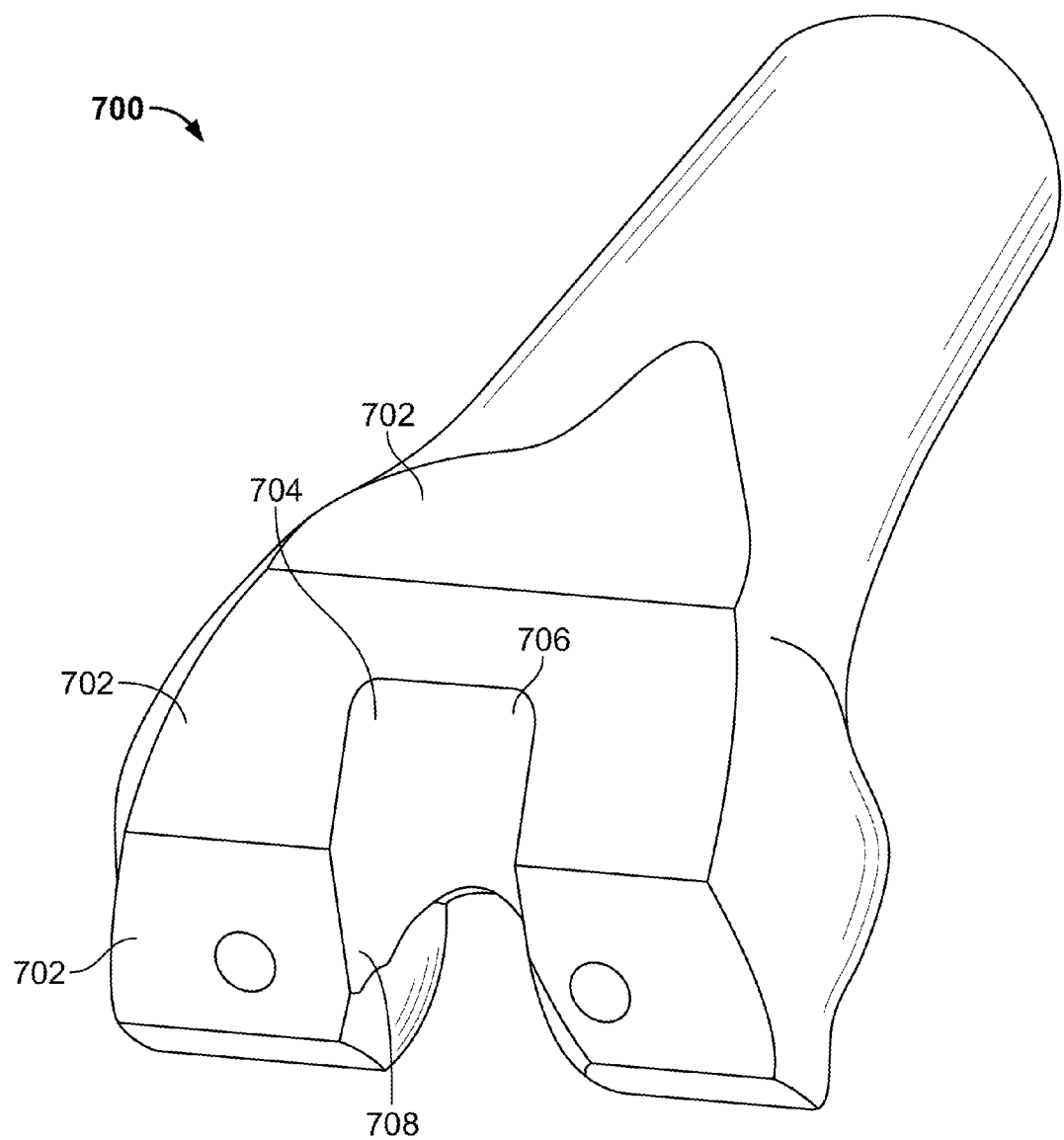
FIG. 17 is a perspective view of a distal femur having a plurality of planar resections and a box cut with radiused edges.

FIG. 17 is a perspective view of a distal femur 700 having a plurality of planar resections 702. Such planar resections are generally referred to as distal, anterior, posterior, and anterior and posterior chamfer cuts. A burr having a certain diameter was used to create radiused corners 704, 706 along inner edges 708 of the resected femur bone. Inner edges 708 with radiused corners 704, 706 correspond to the dimensions of a box of a posterior-stabilized femoral component. The radius of the radiused corners 704, 706 substantially match the radius of the finishing cutter that is used to make the resection.

FIG. 18A is a perspective view of proximal tibia 720 having a resected medial portion 722. The resected medial portion 722 preferably houses at least a portion of an implant that is configured to engage an articular surface of a unicondylar or bi-compartmental femoral implant, for example. The resected medial portion has a radiused corner 724 at the intersection of a transverse wall 725 and a sagittal wall 726 adjacent the tibial eminence as shown in FIG. 18B. Preferably, the radius of the radiused corner 724 substantially matches the radius of the finishing cutter that is used to make the resection.

FIG. 19A is a perspective view of proximal tibia 740 having a resected medial portion 742. The resected medial portion has a radiused corner 744 at the intersection of a transverse wall 745 and a sagittal wall 746 adjacent the tibial eminence as shown in FIG. 19B. Radiused corner 744 runs deeper along sagittal wall 746 than radiused corner 724 shown in FIGS. 18A-B. The radius of the radiused corner 744 substantially matches the radius of the finishing cutter that is used to make the resection; however, the radius of the radius corner 744 may be larger than the radius of the finishing cutter. In such a case, the finishing cutter may make more than one pass in order to create the dimensions of resected radiused corner 744.

FIG. 20A is a perspective view of proximal tibia 760 having a resected portion 762 on medial and lateral sides thereof. Resected portion 762 is formed around the tibial eminence resulting in a tibial plateau 764. The resected portion has radiused corners 767, 768 at the intersection of a transverse wall 765 and a sagittal wall 766 adjacent the tibial eminence as shown in FIG. 20B. The tibial eminence is not resected so as to preserve the anterior and poster cruciate ligaments in a knee arthroplasty procedure. A burr is preferably used to resect a curved recess 770 in the tibial plateau 764. A portion of a corresponding bicruciate retaining implant is configured to engage and be housed at least partially within curved recess 770.

For cementless tibial keel preparation, an interference fit between the tibia and the implant is desired to achieve fixation. The level of interference can preferably be customized using a robot. Preferably, the robot will machine a slot in the tibia, into which a tray will be impacted, and the depth and width of the slot can be tailored to achieve a desired level of interference. For example, a keel slot can be prepared to the full depth of a baseplate keel or to a partial depth to achieve greater interference and pressfit if desired.

For cemented tibial keel preparation, surgeons generally want to ensure there is adequate cement mantle around a tibial baseplate to achieve proper fixation. Using the robot, the size of the cement mantle can be customized by tuning in a desired depth and width of a keel slot.

FIGS. 21A-24C show varying prepared keel slot depths in the proximal tibia. The lesser the depth of the keel slot the greater the interference and pressfit there will be on the baseplate keel of tibial prosthesis when the baseplate keel is inserted into the prepared keel slot and into cancellous bone. The depth of keel slot preparation may be defined as the length of the keel slot from a transverse resection on proximal tibia to an end portion thereof within the tibial shaft measured in a superior to inferior direction, for example.

Sclerotic bone may be found at the outskirts of the width of the baseplate keel of the tibial prosthesis approximately 10-14 mm from the transverse resection of the proximal tibia. Preferably, programming of the robot burr should prepare all of this region to get beyond the sclerotic bone. There is a general desire for quick tibial keel preparation and the shallower the keel preparation, the quicker this part of a procedure will be. Further, with shallower keel preparation there are generally less restrictions on the cutter geometry such as heat generation and debris relief, for example.

FIGS. 21A and 21B are perspective views of a shallow keel slot 802 in a proximal tibia 800. Keel slot 802 includes a central portion 804 flanked by two wing portions 806, 808. As shown in FIG. 21C, keel slot 802 is deeper adjacent the ends of the two wing portions 806, 808 and is shallower in a central region 810. The deeper portions of keel slot 802 are preferably curved forming curved portions 807, 809 while the central region 810 is preferably straight. Keel slot 802 is preferably formed by a 2.5 mm burr while a smaller or larger diameter burr may be used. The depth of the keel slot is approximately ¼ the length of the baseplate keel of the tibia prosthesis that will be implanted in and through the keel slot 802. The depth is measured preferably as a linear distance D1 from the proximal tibia surface 812 to a line tangent to the curved portions 807, 809 of the keel slot 802. The max depth of keel slot 802 is preferably 10.2 mm (0.4 in).

FIGS. 22A and 22B are perspective views of a deeper keel slot 822 in a proximal tibia 820. Keel slot 822 includes a central portion 824 flanked by two wing portions 826, 828. As shown in FIG. 22C, keel slot 822 is deeper adjacent the ends of the two wing portions 826, 828 and is shallower in a central region 830. The deeper portions of the keel slot are preferably curved forming curved portions 827, 829 while the central region 830 is preferably straight. Central region 830 is more prominent that central region 810 of keel slot 802. Keel slot 822 is preferably formed by a 2.5 mm burr while a smaller or larger diameter burr may be used. The depth of keel slot 822 is approximately ½ the length of the baseplate keel of the tibia prosthesis that will be implanted in and through the keel slot 822. The depth is measured preferably as a linear distance D2 from the proximal tibia surface 822 to a line tangent to the curved portions 827, 829 of the keel slot 822. The max depth of keel slot 822 is preferably 14 mm (0.55 in).

Figure 23C:
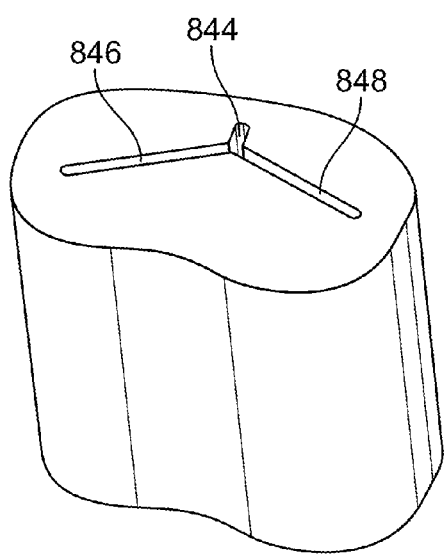
Figure 23C:
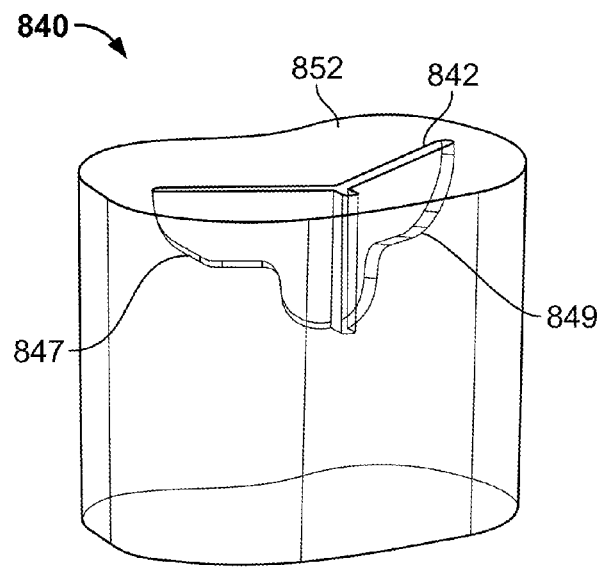
Figure 23C:
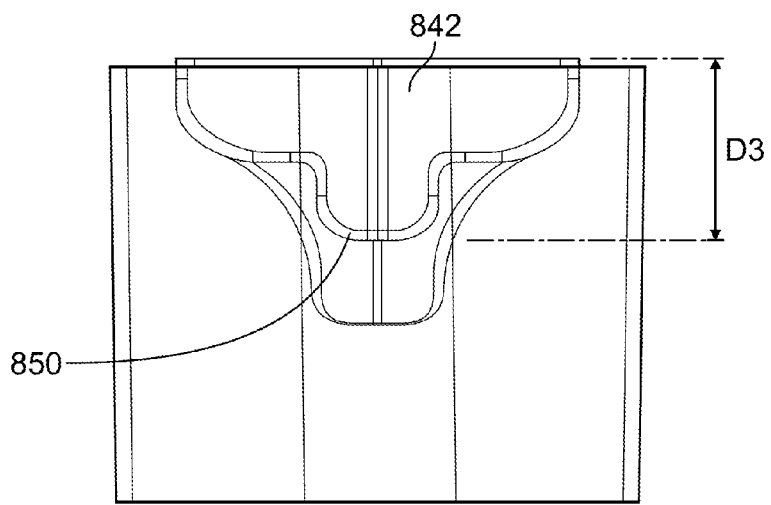

FIGS. 23A and 23B are perspective views of an even deeper keel slot 842 in a proximal tibia 840. Keel slot 842 includes a central portion 844 flanked by two wing portions 846, 848. As shown in FIG. 23C, keel slot 842 is shallower adjacent the ends of the two wing portions 846, 848 and is deeper in a central region 850. The shallower portions of keel slot 842 are preferably curved forming curved portions 847, 849 as well as central region 850. Central region 850 is preferably formed with a lead-in central opening. Keel slot 842 is preferably formed by a 2.5 mm burr while a smaller or larger diameter burr may be used. The depth of keel slot 842 is approximately ¾ the length of the baseplate keel of the tibia prosthesis that will be implanted in and through the keel slot 842. The depth is measured preferably as a linear distance D3 from the proximal tibia surface 842 to a line tangent to the central region 850 of the keel slot 842. The max depth of keel 842 is preferably 23 mm (0.9 in).

FIGS. 24A and 24B are perspective views of an even deeper keel slot 862 in a proximal tibia 860 that the keel slot 842 in proximal tibia 840. Keel slot 862 includes a central portion 864 flanked by two wing portions 866, 868. As shown in FIG. 24C, keel slot 862 is shallower adjacent the ends of the two wing portions 866, 868 and is deeper in a central region 870. The shallower portions of keel slot 862 are preferably curved forming curved portions 867, 869 as well as central region 870. Keel slot 862 is preferably formed by a 2.5 mm burr while a smaller or larger diameter burr may be used. The depth of keel slot 862 is approximately the full length of the baseplate keel of the tibia prosthesis that will be implanted in and through the keel slot 862. The depth is measured preferably as a linear distance D4 from the proximal tibia surface 862 to a line tangent to the central region 870 of the keel slot 862. The max depth of keel slot 862 is preferably 33.5 mm (1.32 in).

Figure 25A:
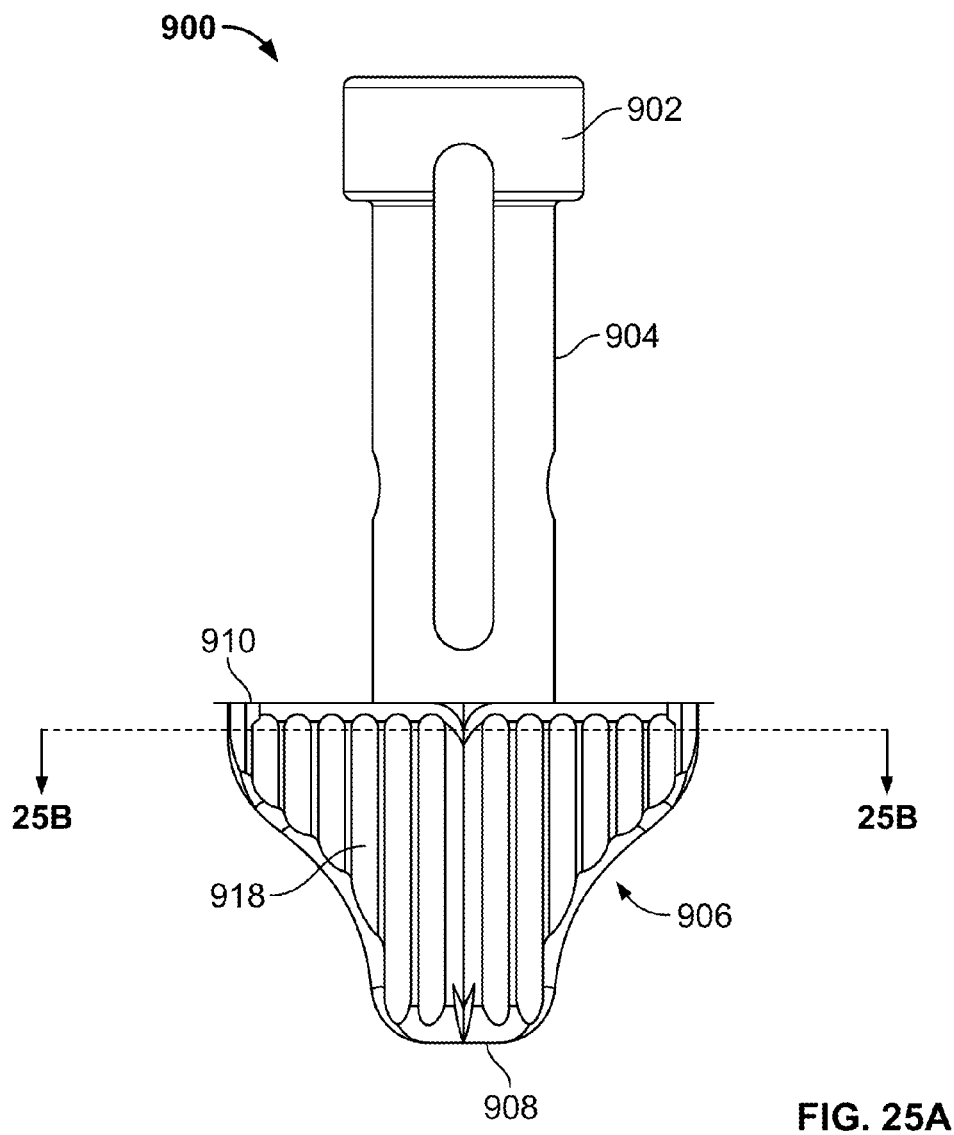
FIG. 25A is a plan view of one embodiment of a keel punch.

FIG. 25A is a plan view of one embodiment of a keel punch 900. Keel punch 900 includes a head portion 902, a shaft portion 904 and a punch portion 906. A distal portion 908 of punch portion 906 is received in a prepared keel slot through the proximal tibia and into cancellous bone until a proximal portion 910 of punch portion 906 is approximately 0.09" from a resected transverse surface on the proximal tibia. A central longitudinal axis of shaft portion 904 is preferably angled 1° from a central longitudinal axis of punch portion 906.

Figure 25B:
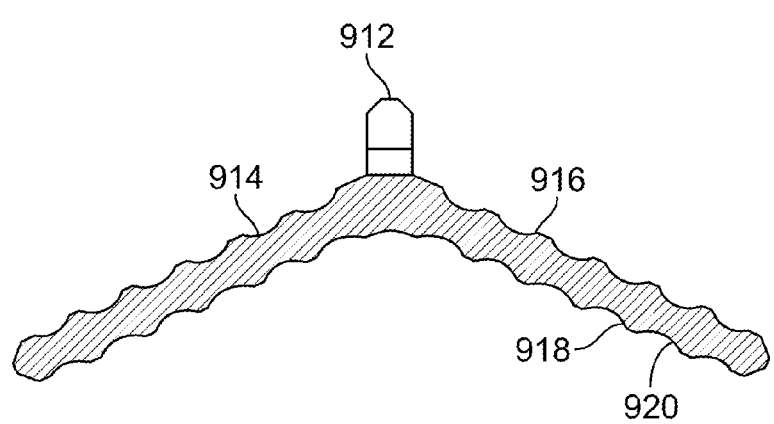
FIG. 25B is a cross-section of the punch portion of the keel punch shown in FIG. 25A taken along line 2-2.

The cross-section of punch portion 900 as shown in section 2-2 of FIG. 25B is substantially similar to the keel slots shown in FIG. 21A-24C. Punch portion 906 includes a central portion 912 flanked by two wing portions 914, 916. As shown in FIG. 25B, the cross-section of punch portion 900 shows striations 918 of punch portion 906 adjacent the proximal portion 910 of punch portion 906. Punch portion 906 includes a plurality of striations 918 which are peak portions along the cross-section of the wing portions 914, 916 of punch portion 906. The plurality of striations 918 are flanked by valley portions 920. Striations 918 are configured to form an interference fit with the bone of the proximal tibia while valley portions 920 are configured to form relief portions that may either be clearance or interference portions.

A traditional keel punch as shown in FIG. 25A, for example, leaves a keel slot adjacent the transverse surface of the proximal tibia having a cross-section generally as shown in FIG. 25B, for example. The cross-section as shown in FIG. 25B may be modified using a burr having a particular diameter following a particular tool path. The following embodiments discuss the different levels of clearance and interference between certain burr sizes and tool paths used to create a keel slot in the proximal tibia.

Figure 26A:
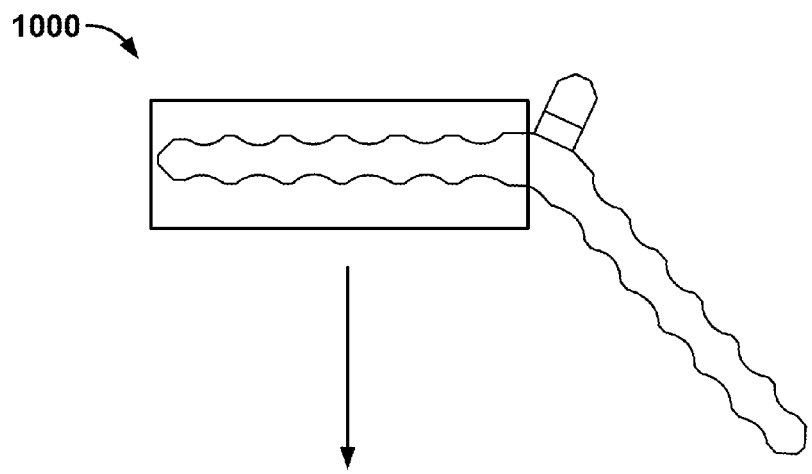
FIG. 26A is a cross-section of another embodiment of a punch portion of a keel punch adjacent the proximal end of the punch portion.
Figure 26B:
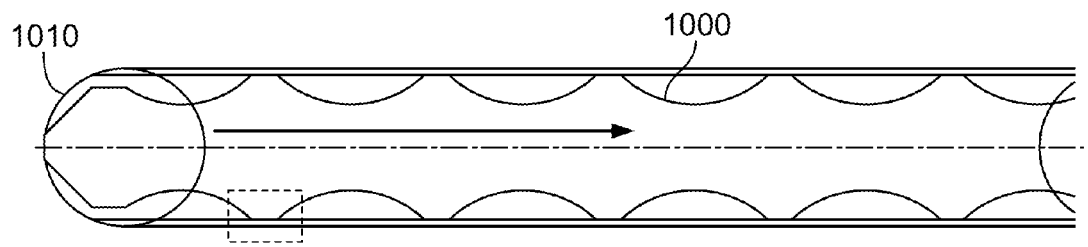
FIG. 26B shows the difference in cross-section between a 3 mm burr straight cut and the cross-section of the portion of the punch portion of the keel punch shown in FIG. 26A.
Figure 26C:
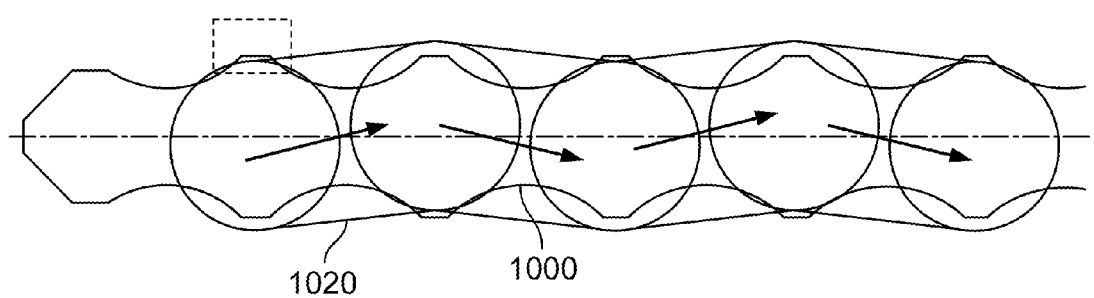
FIG. 26C shows the difference in cross-section between a 3 mm burr wave cut and the cross-section of the portion of the punch portion of the keel punch shown in FIG. 26A.

FIG. 26A is an example of a cross-section 1000 of a punch portion of a keel punch adjacent the proximal end of the punch portion. FIG. 26B shows the difference in cross-section between a 3 mm burr straight cut 1010 and the cross-section 1000 of a portion of the punch portion of the keel punch shown in FIG. 26A. The 3 mm burr straight cut 1010 provides approximately 0.0035" clearance with a tibial prosthesis, which provides less interferences with the tibial prosthesis compared to conventional tibial resection using the keel punch. FIG. 26C shows the difference in cross-section between a 3 mm burr wave cut 1020 and the cross-section 1000 of a portion of the punch portion of the keel punch shown in FIG. 26A. The 3 mm burr wave cut 1020 follows the direction of the arrows in alternating posterior and anterior directions. The 3 mm burr wave 1020 cut provides approximately 0.011" clearances and 0.004" interferences at a minimum with the tibial prosthesis, which provides greater clearances and lesser interferences with the tibial prosthesis compared to 3 mm burr straight cut 1010 shown in FIG. 26B.

Figure 27A:
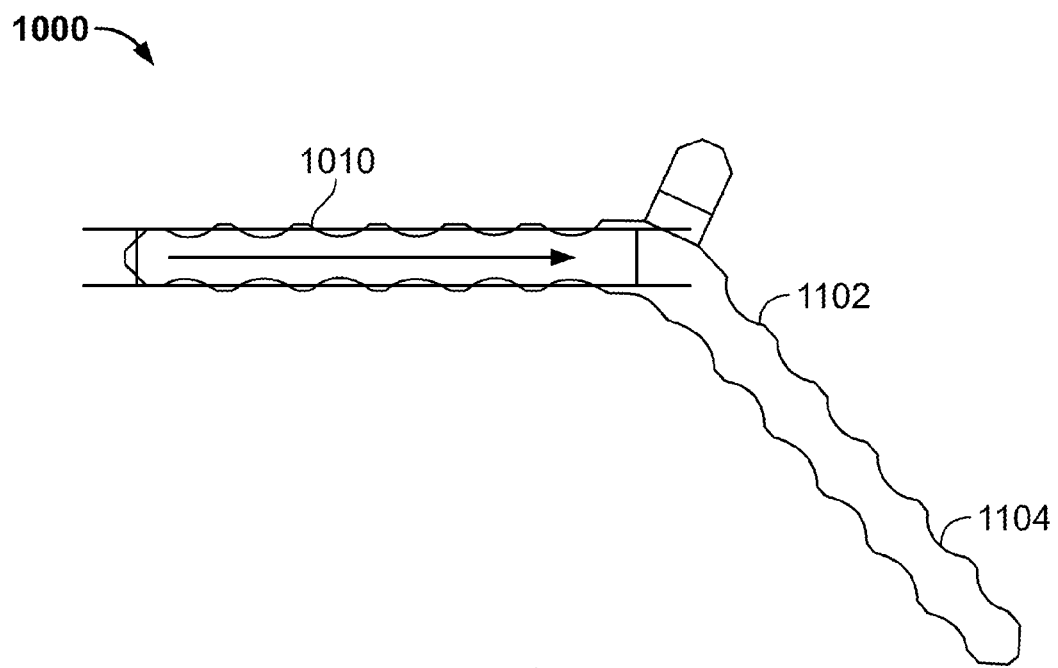
FIG. 27A is an example of a cross-section of another embodiment of a punch portion of a keel punch adjacent the proximal end of the punch portion.

FIG. 27A is an example of a cross-section 1100 of a punch portion of a keel punch adjacent the proximal end of the punch portion. FIG. 27A also shows a 2.5 mm burr straight cut 1110 overlay on cross-section 1100. The punch portion of the keel punch shown includes a plurality of alternating major striations 1102 and minor striations 1104 and the interference and clearance differences at the locations of the major and minor striations in relation to a conventional keel punch. As explained above, major and minor striations 1102, 1104 are alternating peaks and valley portions, respectively.

Major striations 1102 are portions on the punch portion of the keel punch that provide relatively greater interference with a corresponding keel of a tibial prosthesis than are provided by minor striations 1104, if at all. For instance, major striations 1102 generally provide interference with a corresponding keel of a tibial prosthesis, while minor striations 1104 generally provide no interference, but instead provide clearance with a corresponding keel of a tibial prosthesis.

Figure 27B:
FIG. 27B is a cross-sectional view at Section 1-1 of FIG. 27A of a 2.5 mm burr straight cut in relation to a major striation of the keel punch of FIG. 27A.
Figure 27C:
FIG. 27C is a cross-sectional view at Section 2-2 of FIG. 27A of the 2.5 mm burr straight cut in relation to the minor striation of the keel punch of FIG. 27A.

As shown in FIG. 27B, there is a cross-sectional view at Section 1-1 of FIG. 27A of the 2.5 mm burr straight cut 1110 in relation to the major striation 1102 of the conventional keel punch. There is an added 0.007" interference difference created with the 2.5 mm burr straight cut 1110 in relation to the interference created by the major striation 1102 of the conventional keel punch at Section 1-1. Using the 2.5 mm burr straight cut 1110, there will result in greater interferences with the keel of the tibial prosthesis at the major striations thereof compared to the resulting interferences created with convention keel punch preparation. FIG. 27C there is a cross-sectional view at Section 2-2 of FIG. 27A of the 2.5 mm burr straight cut 1110 in relation to the minor striation 1104 of the conventional keel punch. As shown, there is a 0.012" clearance difference created between the 2.5 mm burr straight cut 1110 in relation to the clearance created by the minor striation 1104 of the conventional keel punch at Section 2-2. Using the 2.5 mm burr straight cut 1110, there will result in lesser clearances (i.e. greater interferences) with the keel of the tibial prosthesis at the minor striations thereof compared to the resulting clearances created with conventional keel punch preparation.

Figure 28A:
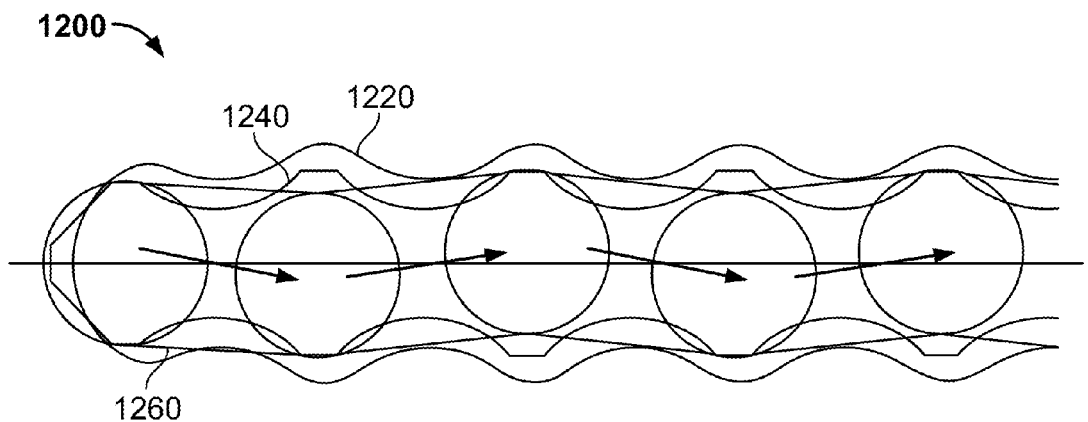
FIGS. 28A-28B are examples of a transverse cross-section of a tibial prosthesis keel, a punch portion of a keel punch, and a 2.5 mm burr wave cut.
Figure 28B:
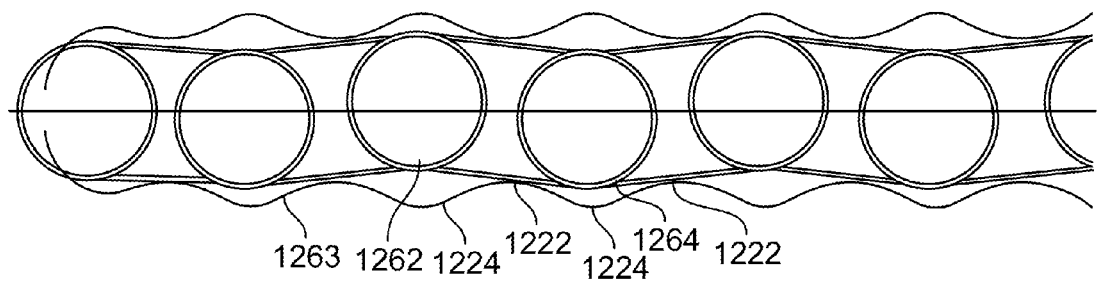

FIG. 28A is an example of a transverse cross-section 1200 of a tibial prosthesis keel 1220, a punch portion 1240 of a keel punch, and a 2.5 mm burr wave cut 1260. FIG. 28A shows the differences in interferences and clearances created between each of the punch portion 1240 and 2.5 mm burr wave cut 1260 in relation to the tibial prosthesis keel 1220. FIG. 28B shows that the 2.5 mm burr wave cut 1260 results in alternating 0.014" and 0.028" interferences between alternating peaks 1264 and valleys 1262 of the 2.5 mm burr wave cut 1260, respectively, in relation to alternating major striations 1224 of the tibial prosthesis keel 1220. Further, the 2.5 mm burr wave cut 1260 results in less than a 0.002" interference between an intermediate portion 1263 of the 2.5 mm burr wave cut 1260 located between the alternating peaks 1264 and valleys 1262 thereof and the minor striations 1224 of the tibial prosthesis keel 1220.

Figure 29A:
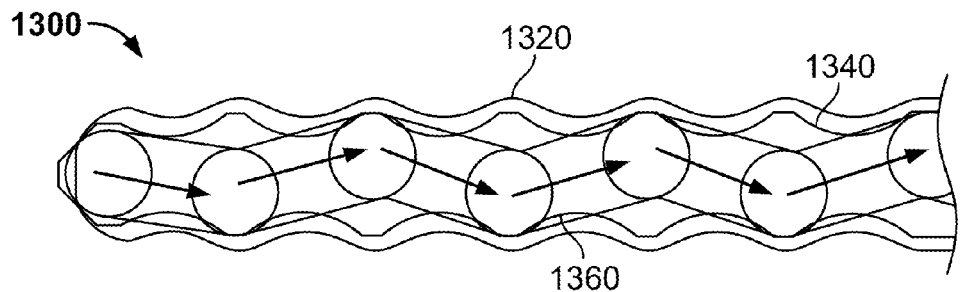
FIGS. 29A-29B are examples of a transverse cross-section of a tibial prosthesis keel, a punch portion of a keel punch, and a 2.0 mm burr wave cut.
Figure 29B:
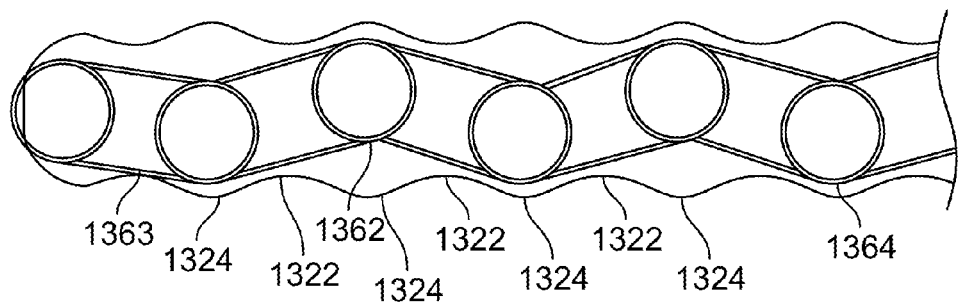

FIG. 29A is an example of a transverse cross-section 1300 of a tibial prosthesis keel 1320, a punch portion 1340 of a keel punch, and a 2.0 mm burr wave cut 1360. FIG. 29A shows the differences in interferences and clearances created between each of the punch portion 1340 and 2.0 mm burr wave cut 1360 in relation to the tibial prosthesis keel 1320. FIG. 29B shows that the 2.0 mm burr wave cut 1360 results in alternating 0.014" and 0.048" interferences between alternating peaks 1364 and valleys 1362 of the 2.0 mm burr wave cut 1360, respectively, in relation to alternating major striations 1324 of the tibial prosthesis keel 1320. Further, the 2.0 mm burr wave cut 1360 results in less than a 0.002" interference between an intermediate portion 1363 of the 2.0 mm burr wave cut 1360 located between the alternating peaks 1364 and valleys 1362 thereof and the minor striations 1324 of the tibial prosthesis keel 1320.

Figure 30A:
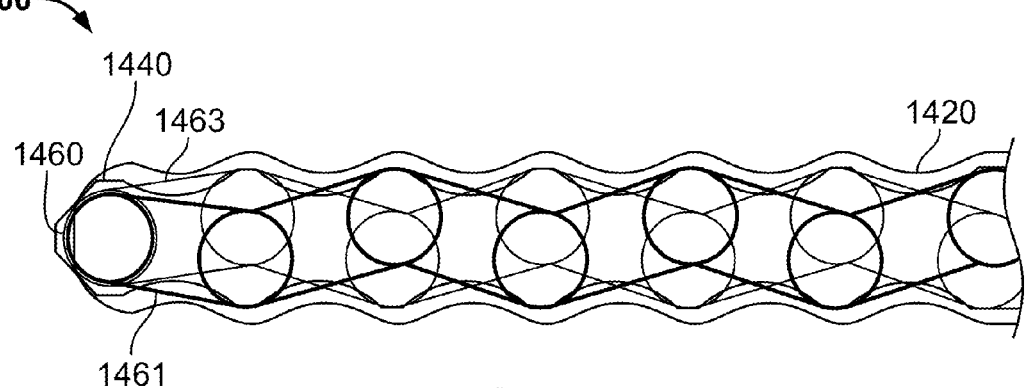
FIGS. 30A-30B are examples of a transverse cross-section of a tibial prosthesis keel, a punch portion of a keel punch, and a 2.0 mm burr double wave cut including a first wave cut and a second wave cut.

FIG. 30A is an example of a transverse cross-section 1400 of a tibial prosthesis keel 1420, a punch portion 1440 of a keel punch, and a 2.0 mm burr double wave cut 1460 including a first wave cut 1461 and a second wave cut 1463.

Figure 30B:
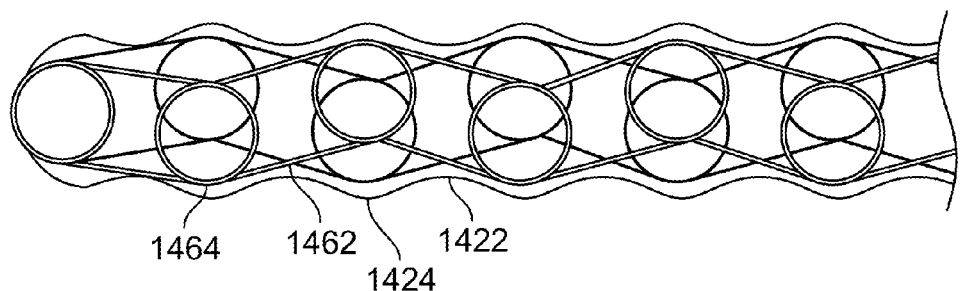

First and second wave cuts 1461, 1463 travel along the length of each cut in alternating anterior and posterior directions. FIG. 30A shows the differences in interferences and clearances created between each of the punch portion 1440 and 2.0 mm burr double wave cut 1460 in relation to the tibial prosthesis keel 1420. FIG. 30B shows that the 2.0 mm burr double wave cut 1460 results in alternating 0.014" and 0.012" interferences between alternating peaks 1464 and valleys 1462 of the 2.0 mm burr double wave cut 1460, respectively, in relation to alternating major striations 1424 and minor striations 1422 of the tibial prosthesis keel 1420, respectively.

Figure 31A:
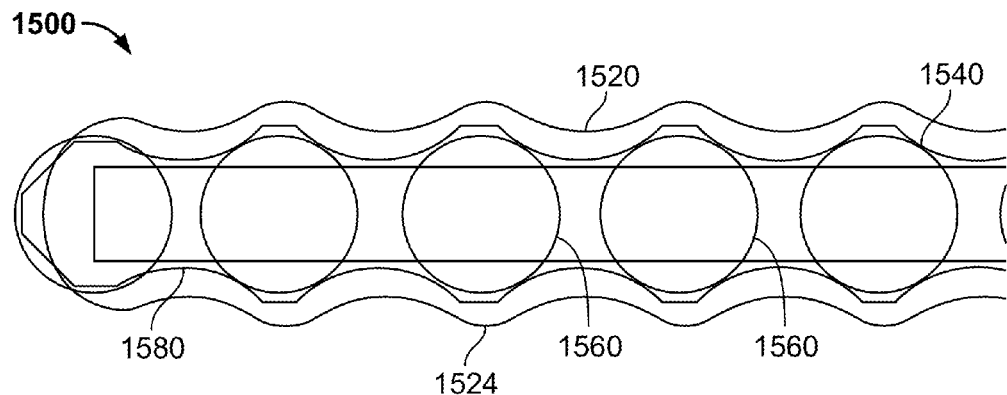
FIGS. 31A-31B are examples of a transverse cross-section of a tibial prosthesis keel, a punch portion of a keel punch, and successive 2.5 mm burr plunge cuts located at each major striation of tibial prosthesis keel and a 1.5 mm burr straight cut.
Figure 31B:
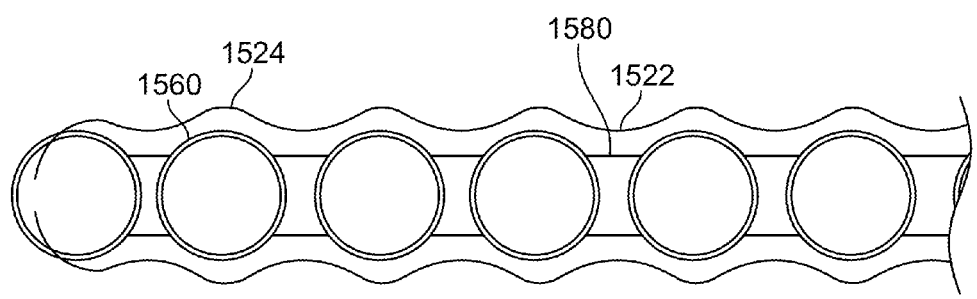

FIG. 31A is an example of a transverse cross-section 1500 of a tibial prosthesis keel 1520, a punch portion 1540 of a keel punch, and successive 2.5 mm burr plunge cuts 1560 located at each major striation 1524 of tibial prosthesis keel 1520 and a 1.5 mm burr straight cut 1580. FIG. 31A shows the differences in interferences and clearances created between each of the punch portion 1540 and successive 2.5 mm burr plunge cuts 1560 located at each major striation 1524 of tibial prosthesis keel 1520 and a 1.5 mm burr straight cut 1580 in relation to the tibial prosthesis keel 1520. FIG. 31B shows that the successive 2.5 mm burr plunge cuts 1560 located at each major striation 1524 of tibial prosthesis keel 1520 result in a 0.021" interference with each major striation 1524 of tibial prosthesis keel 1520. Also shown in FIG. 31B is that at each minor striation 1522 of tibial prosthesis keel 1520 there is a 0.023" interference with the 1.5 mm burr straight cut 1580.

Figure 32A:
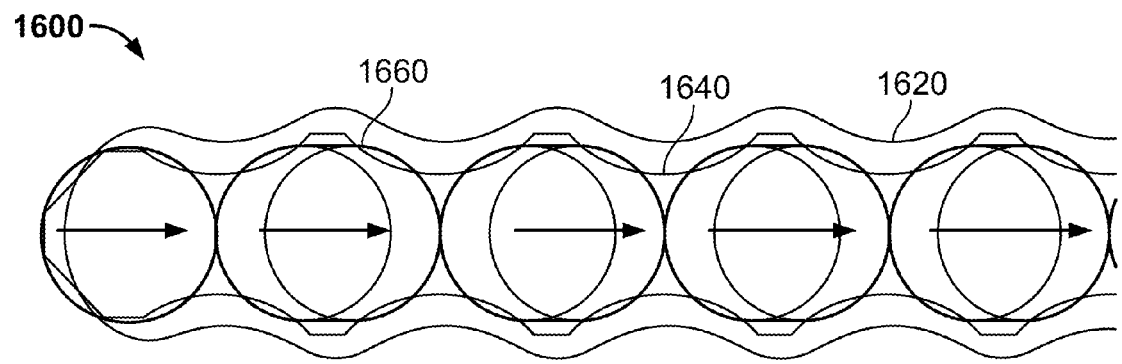
FIGS. 32A-32C are examples of a transverse cross-section of a tibial prosthesis keel, a punch portion of a keel punch, and successive 2.5 mm burr plunge and drag cuts.
Figure 32B:
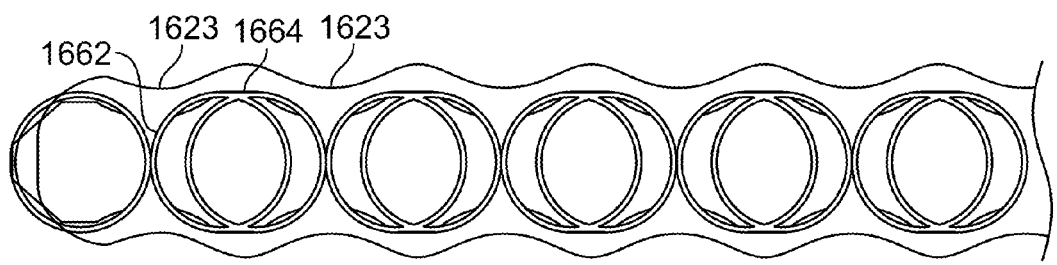
Figure 32C:
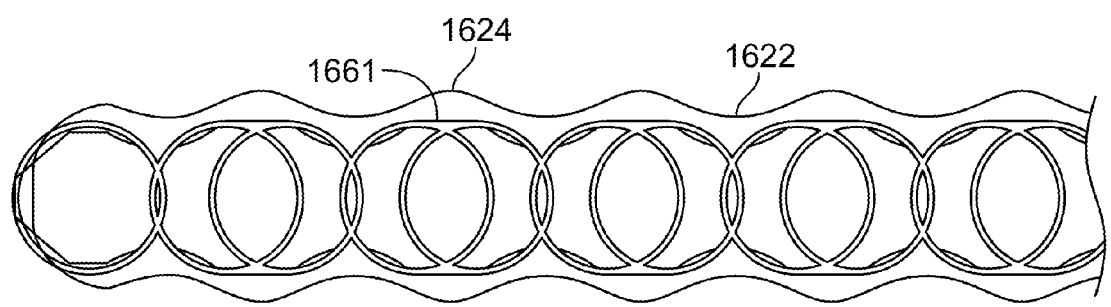

FIG. 32A is an example of a transverse cross-section 1600 of a tibial prosthesis keel 1620, a punch portion 1640 of a keel punch, and successive 2.5 mm burr plunge and drag cuts 1660. A central axis of the plunge of the 2.5 mm burr is preferably located adjacent an intermediate portion 1623 thereof located between an adjacent minor striation 1622 and major striation 1624 of the tibial prosthesis keel 1620. The length of the drag of the 2.5 mm burr in a medial to lateral direction (or vice versa depending on whether the left or right tibia is being resected) is the distance between adjacent intermediate portions 1623 along the length of the tibial prosthesis keel 1620. FIG. 31A shows the differences in interferences and clearances created between each of the successive 2.5 mm burr plunge and drag cuts 1660 in relation to the tibial prosthesis keel 1520. FIG. 32B shows that the maximum interference between the minimum striation 1662 created between successive 2.5 mm burr plunge and drag cuts 1660 and the minor striation 1622 of the tibial prosthesis keel 1620 is 0.052" (depending on amount of plunge overlap between successive 2.5 mm burr plunge and drag cuts 1660). FIG. 32C shows that the minimum interference between the maximum striation 1664 created between successive 2.5 mm burr plunge and drag cuts 1660 and the maximum striation 1624 of the tibial prosthesis keel 1620 is 0.021".

Figure 33A:
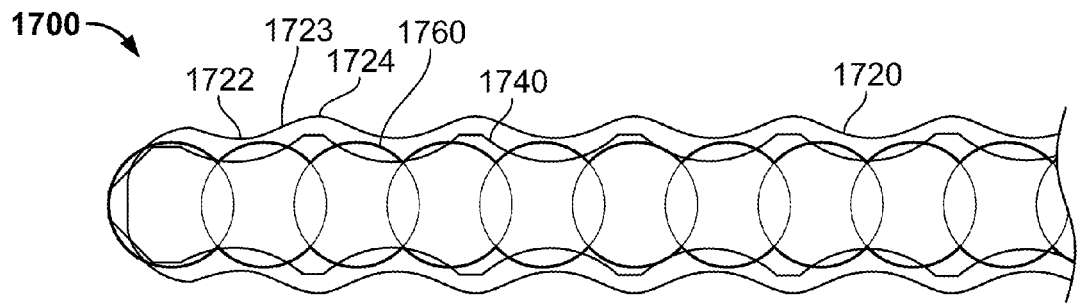
FIGS. 33A-33B are examples of a transverse cross-section of a tibial prosthesis keel, a punch portion of a keel punch, and successive 2.5 mm burr plunge cuts.
Figure 33B:
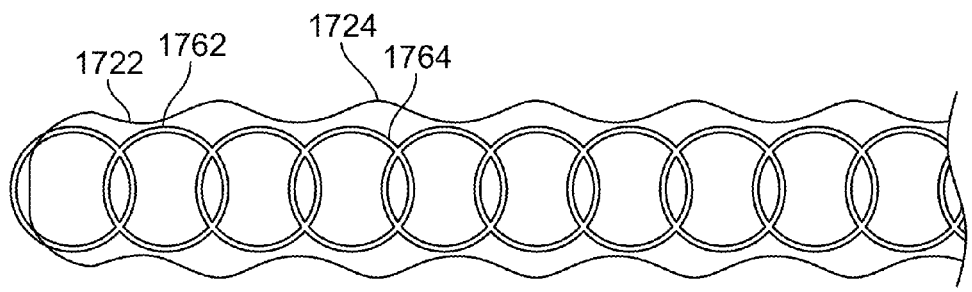

FIG. 33A is an example of a transverse cross-section 1700 of a tibial prosthesis keel 1720, a punch portion 1740 of a keel punch, and successive 2.5 mm burr plunge cuts 1760. A central axis of each of the successive 2.5 mm burr plunge cuts 1760 is preferably located adjacent an intermediate portion 1723 located between an adjacent minor striation 1722 and major striation 1724 of the tibial prosthesis keel 1720. Successive central axes of 2.5 mm burr plunge cuts 1760 are preferably at least 0.065" apart from one another. FIG. 33A shows the differences in interferences and clearances created between each of the punch portion 1740 and successive 2.5 mm burr plunge cuts 1760 in relation to the tibial prosthesis keel 1720. FIG. 33B shows that the successive 2.5 mm burr plunge cuts 1760 located at a major striation 1724 of tibial prosthesis keel 1720 results in a maximum 0.037" interference with a minor striation 1764 of the successive 2.5 mm burr plunge cuts 1760. Also shown in FIG. 33B is that minor striations 1722 of tibial prosthesis keel 1720 there is a minimum 0.003" interference with a major striation 1762 of the successive 2.5 mm burr plunge cuts 1760.

Figure 34A:
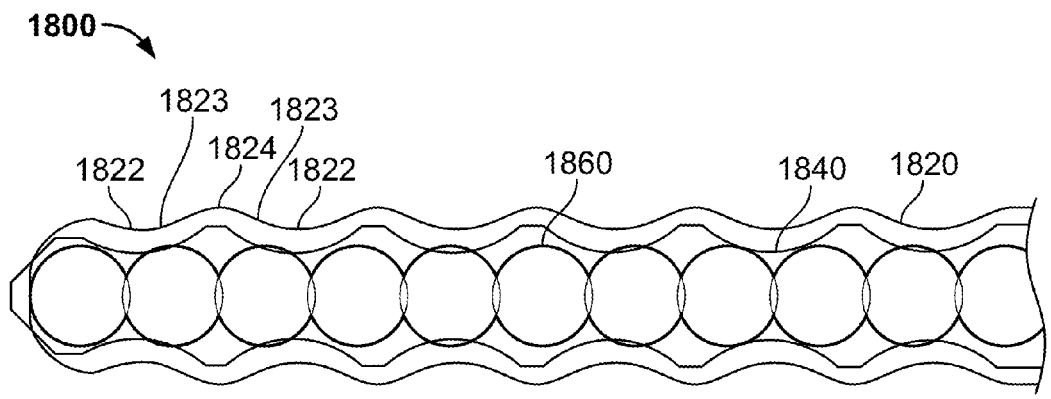
FIGS. 34A-34B are examples of a transverse cross-section of a tibial prosthesis keel, a punch portion of a keel punch, and successive 2.0 mm burr plunge cuts.
Figure 34B:
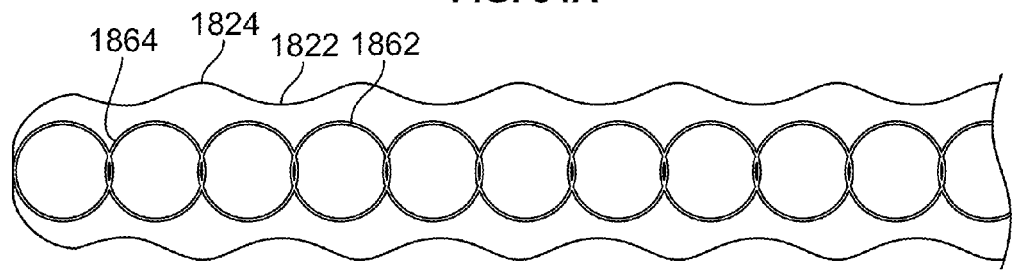

FIG. 34A is an example of a transverse cross-section 1800 of a tibial prosthesis keel 1820, a punch portion 1840 of a keel punch, and successive 2.0 mm burr plunge cuts 1860. A central axis of each of the successive 2.0 mm burr plunge cuts 1860 is preferably located adjacent an intermediate portion 1823 located between an adjacent minor striation 1822 and major striation 1824 of the tibial prosthesis keel 1820. Successive central axes of 2.0 mm burr plunge cuts 1860 are preferably at least 0.030" apart from one another. FIG. 34A shows the differences in interferences and clearances created between each of the punch portion 1840 and successive 2.0 mm burr plunge cuts 1860 in relation to the tibial prosthesis keel 1820. FIG. 34B shows that the successive 2.0 mm burr plunge cuts 1860 located at a major striation 1824 of tibial prosthesis keel 1820 results in a maximum 0.055" interference with a minor striation 1864 of the successive 2.0 mm burr plunge cuts 1860. Also shown in FIG. 34B is that minor striations 1822 of tibial prosthesis keel 1820 there is a minimum 0.013" interference with a major striation 1862 of the successive 2.0 mm burr plunge cuts 1860.

Figure 35A:
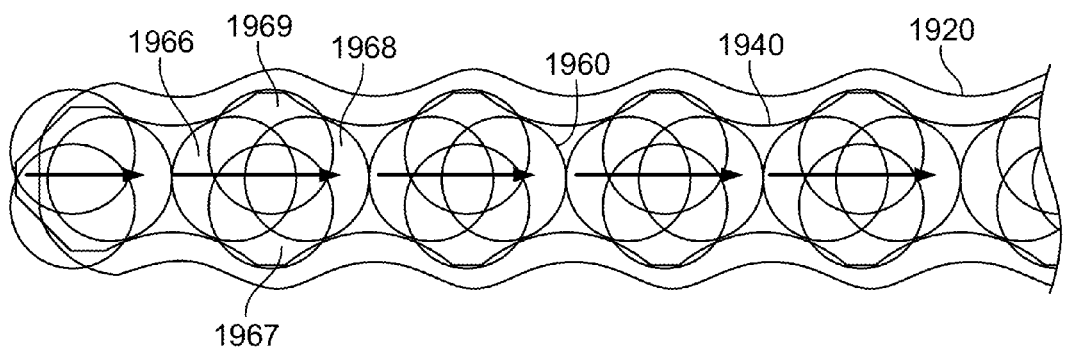
FIGS. 35A-35C are examples of a transverse cross-section of a tibial prosthesis keel, a punch portion of a keel punch, and successive 2.0 mm burr plunge diamond cuts each including first, second, third and forth plunge cuts.
Figure 35B:
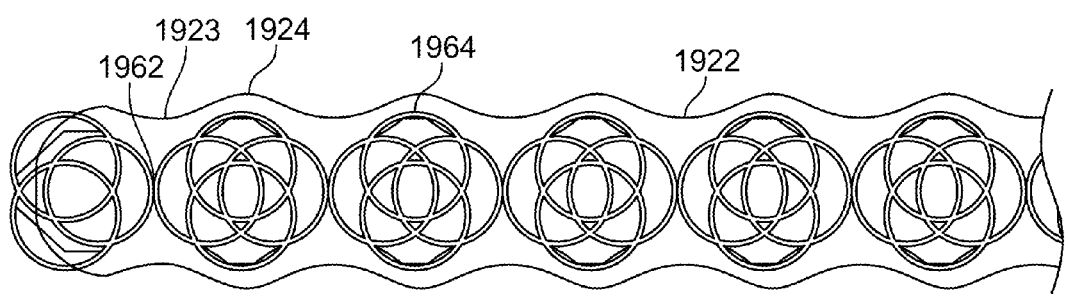
Figure 35C:
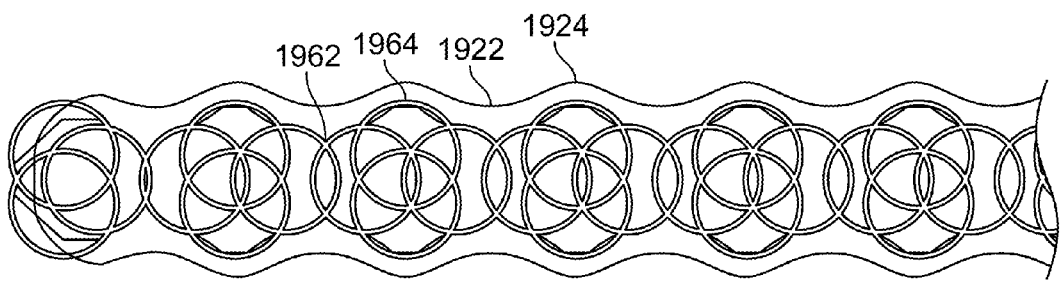

FIG. 35A is an example of a transverse cross-section 1900 of a tibial prosthesis keel 1920, a punch portion 1940 of a keel punch, and successive 2.0 mm burr plunge diamond cuts 1960 including first, second, third and forth plunge cuts 1966, 1967, 1968 and 1969, respectively. A central axis of first plunge cut 1966 of the 2.0 mm burr for each diamond cut is preferably located adjacent an intermediate portion 1923 located between an adjacent minor striation 1922 and major striation 1924 of the tibial prosthesis keel 1920. The second, third and forth plunge cuts are then created in a clockwise or counterclockwise fashion from first plunge cut 1966. FIGS. 35B and 35C show the differences in interferences and clearances created between each of the successive 2.0 mm burr plunge diamond cuts 1960 in relation to the tibial prosthesis keel 1620. FIG. 35B shows that the maximum interference between the minimum striation 1962 created between successive 2.0 mm burr plunge diamond cuts 1960 and the minor striation 1922 of the tibial prosthesis keel 1920 is 0.052" (depending on amount of plunge overlap between successive 2.0 mm burr plunge diamond cuts 1960). FIG. 35C shows that the minimum interference between the maximum striation 1964 created between successive 2.0 mm burr plunge diamond cuts 1960 and the maximum striation 1924 of the tibial prosthesis keel 1920 is 0.013".

Figure 36A:
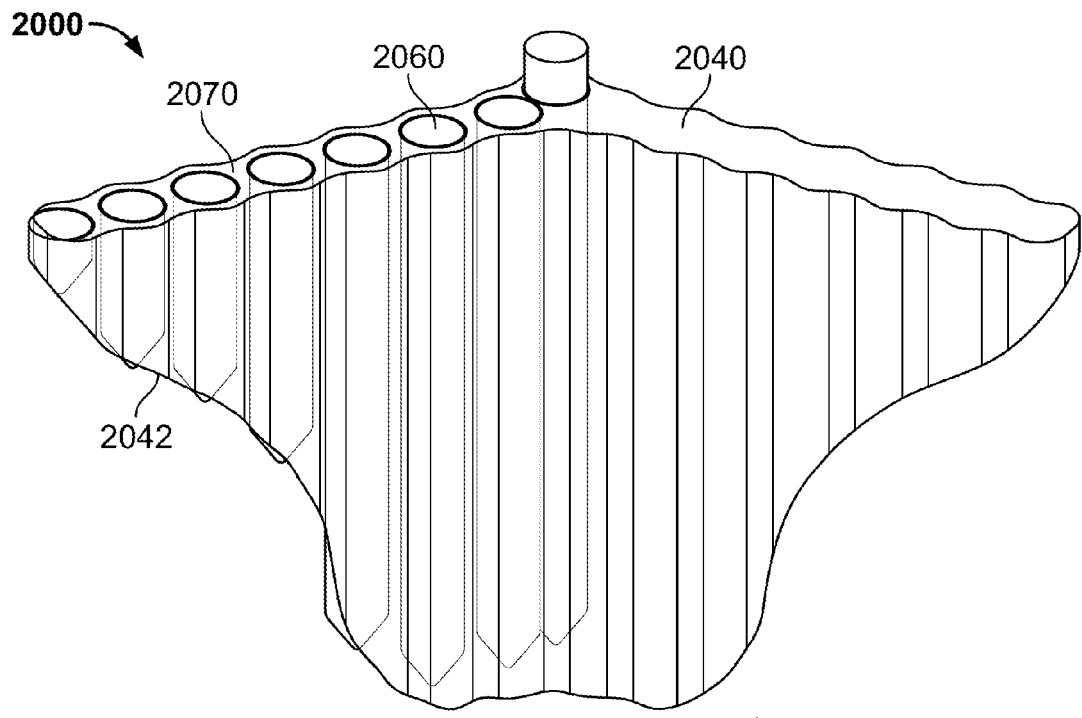
FIG. 36A is a perspective view of a punch portion of a keel punch with successive 2.5 mm drilled holes and 2.0 mm burr plunge cuts in between each 2.5 mm drilled holes following the path of an outer perimeter surface of the punch portion.
Figure 36B:
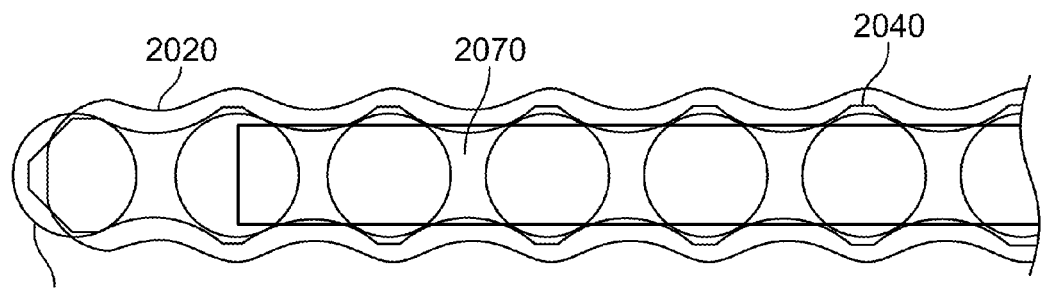
FIGS. 36B-36C are examples of a transverse cross-section of the tibial prosthesis keel, the punch portion of the keel punch, and the 2.5 mm drilled holes and 2.0 mm burr plunge cuts in between each 2.5 mm drilled holes.
Figure 36C:
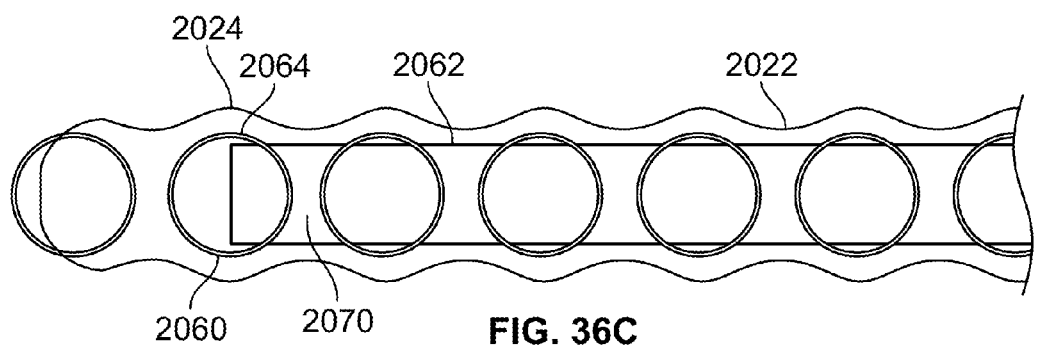

FIG. 36A is a perspective view of a punch portion 2040 of a keel punch with successive 2.5 mm drilled holes 2060 and 2.0 mm burr plunge cuts 2070 in between each 2.5 mm drilled holes 2060 following the path of an outer perimeter surface 2042 of the punch portion. The depth of the 2 mm burr plunge cuts 2070 preferably are at a constant offset of approximately 8 mm from the outer perimeter surface 2042 of the punch portion. This offset allows for bone compression and interference when a tibial prosthesis keel 2020 is fully received in the prepared resection using this multi-cut strategy. FIG. 36B is an example of a transverse cross-section 2000 of the tibial prosthesis keel 2020, the punch portion 2040 of the keel punch, and the 2.5 mm drilled holes 2060 and 2.0 mm burr plunge cuts 2070 in between each 2.5 mm drilled holes 2060. A central axis of each of the successive 2.5 mm drilled holes 2060 is preferably located adjacent a major striation 2024 of the tibial prosthesis keel 2020. FIG. 36C shows that the successive 2.5 mm drilled holes 2060 located adjacent major striations 2024 of tibial prosthesis keel 2020 result in approximately 0.021" interference with a major striation 2064 of the successive 2.5 mm drilled holes 2060. Also shown in FIG. 36B is that minor striations 2022 of tibial prosthesis keel 2020 there is approximately 0.013" interference created between a minor striation 2062 of the 2 mm burr plunge cuts 2060.

FIG. 37A is a perspective view of a punch portion 2140 of a keel punch with successive 2.5 mm drill pivot cuts 2160 following the path of an outer perimeter surface 2142 of the punch portion. The 2.5 mm drill shown in FIG. 37B removes material in the proximal tibia by pivoting on a point fixed at a distal end of the desired depth following what would be the outer perimeter surface 2142 of the punch portion. Each pivot cut includes three separate plunge cuts having an axis approximately 10° from each successive plunge. Each successive plunge cut can be more or less than 10° depending on the interference desired between the resection created and a corresponding tibial prosthesis keel such as prosthesis keel 2120. FIG. 37C is an example of a transverse cross-section 2100 of the tibial prosthesis keel 2120, the punch portion 2140 of the keel punch, and the 2.5 mm drill pivot cuts 2160. As shown in FIGS. 37C-D, a central axis of each pivot cut 2160 is preferably located adjacent a major striation 2124 of the tibial prosthesis keel 2120. FIG. 37D shows that the successive 2.5 mm drill pivot cuts 2160 located adjacent major striations 2124 of tibial prosthesis keel 2120 result in approximately 0.021" interference with a major striation 2164 of the successive 2.5 mm drill pivot cuts 2160. Also shown in FIG. 37D is that there is approximately 0.045" interference created between a minor striation 2162 of the successive 2.5 mm drill pivot cuts 2160 and minor striations 2122 of tibial prosthesis keel 2120.

Figure 38A:
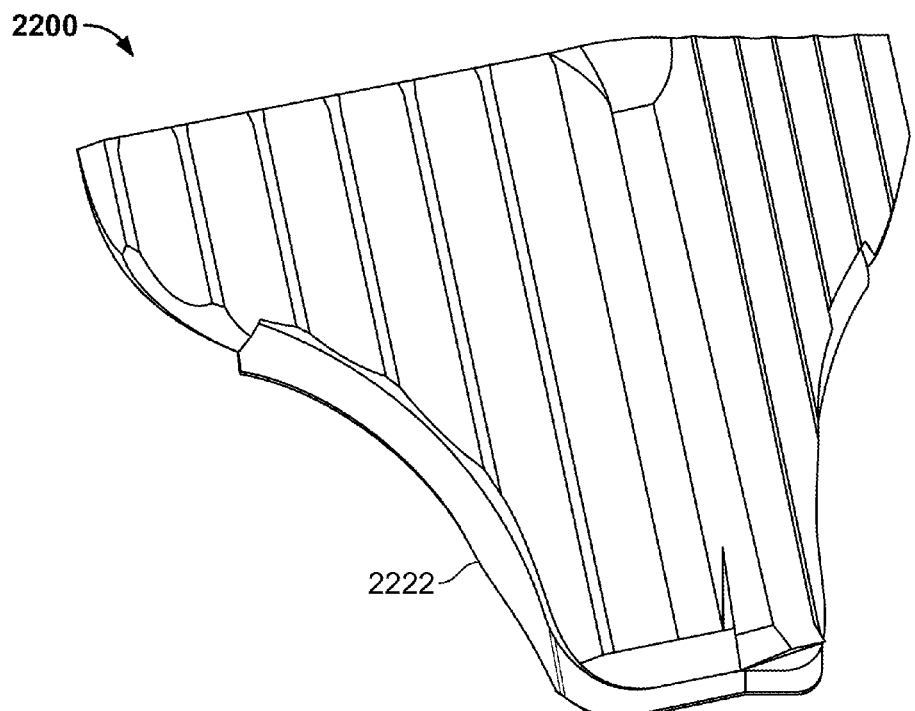
FIG. 38A is a perspective view of an embodiment of a tibial prosthesis keel having a custom keel shape around a portion of an outer perimeter thereof.
Figure 38B:
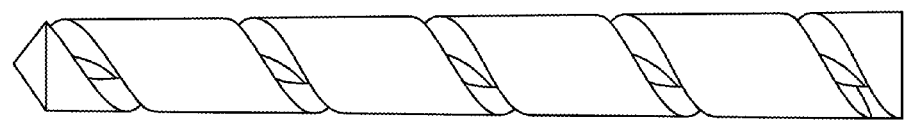
FIG. 38B is an embodiment of a 0.5° drafted end mill.

FIG. 38A is a perspective view of an embodiment of a tibial prosthesis keel 2220 having a custom keel shape around a portion of an outer perimeter 2222 thereof. FIG. 38B is an embodiment of a 0.5° drafted end mill 2240. The custom keel shape shown in FIG. 38A can be prepared using multiple plunge cuts with end mill 2240. Leading edge cuts are made using end mill 2240 while following shape of outer perimeter 2222 of tibial prosthesis keel 2220. Such cuts will compress cancellous bone for receipt of tibial prosthesis keel 2220 creating a greater compression fit.

Prior to finishing off certain bone cuts with an accurate cut using a burr and robot, for example, debulking is generally performed to remove a majority of bone as a first pass before such a finishing pass is performed. While debulking is performed to remove a majority of bone, a sufficient amount of bone must be preserved such that subsequent adjustments to all degrees of freedom of an implant that will be implanted on the resected surface can still be done. In a finishing pass, 1-2 mm layer of remaining bone on all cut surfaces is removed. Final adjustments to implant position and shape is made during a finishing pass. This may include a scalloped surface finish for receipt of certain shaped implants.

Figure 39A:
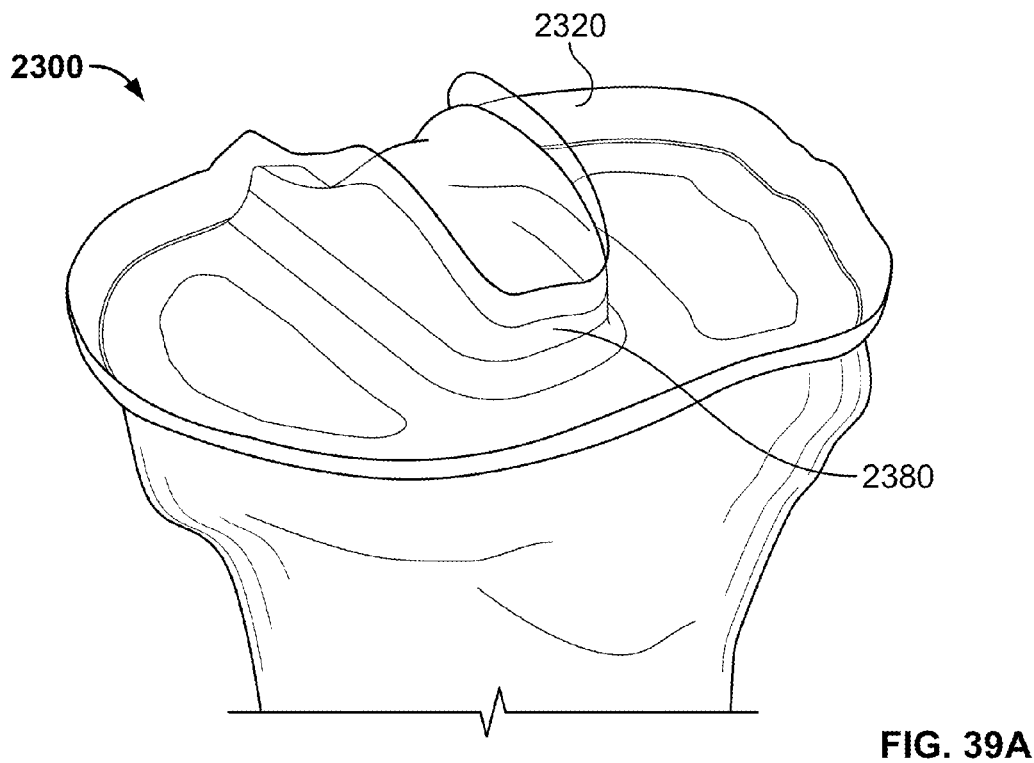
FIGS. 39A-39B are perspective views of the proximal tibia after bicruciate retaining debulking and finishing is performed.
Figure 39B:
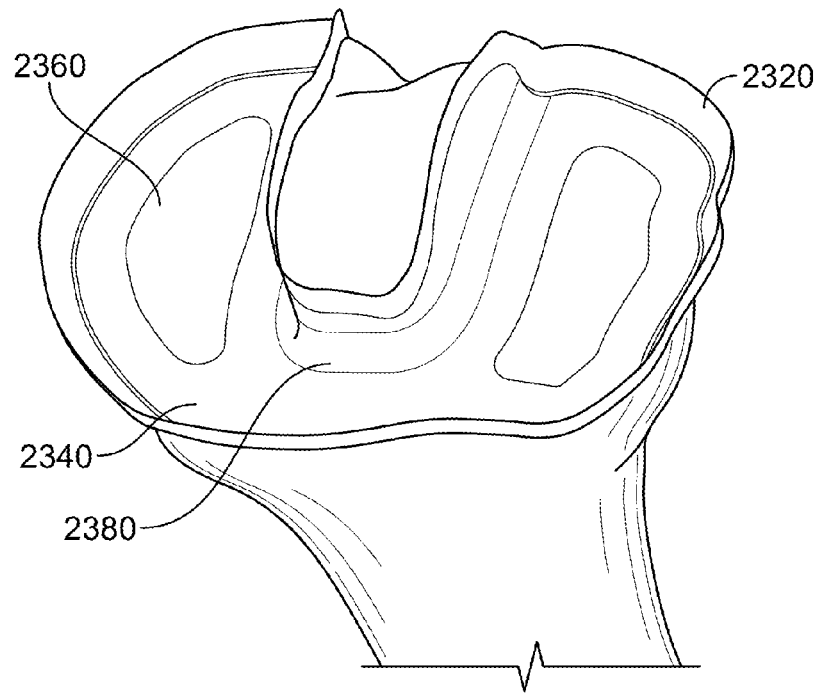
Figure 39C:
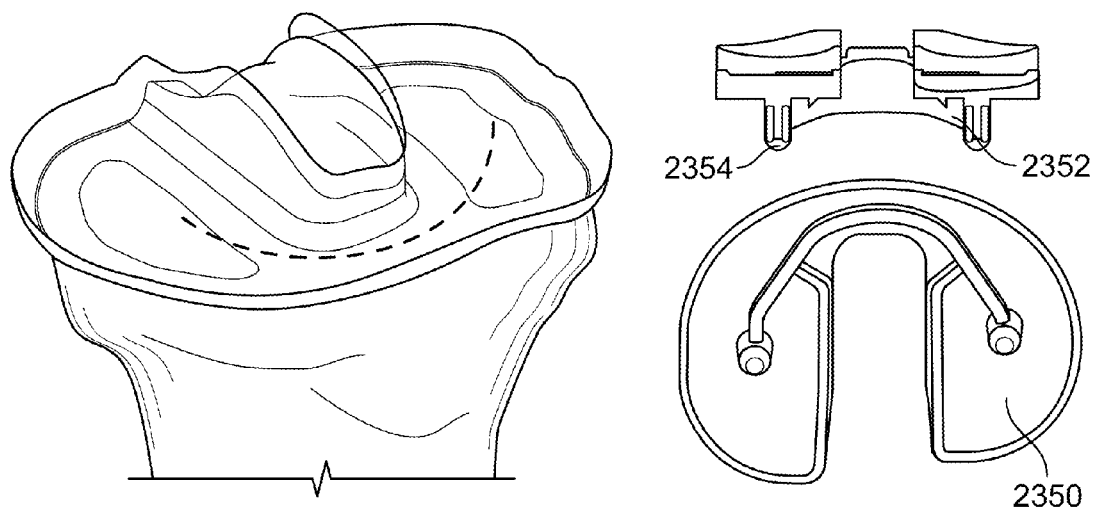
FIG. 39C shows a tibial implants having a keel and pegs configured to be retained within a slot machined into proximal tibia prepared surface shown in FIGS. 39A-39B.

FIGS. 39A and 39B are perspective views of the proximal tibia 2300 after bicruciate retaining debulking and finishing is performed. As shown there is an outer tool boundary region 2320, a cortical rim region 2340 and a cancellous bone region 2360. These regions may vary in size depending on the diameter of the debulking cutter used. For example, a 3, 4 or 5 mm diameter debulking cutter may be used to create the debulking cutter radius all around the proximal tibia as shown in tool boundary region 2320. Preferably, a 3.2 mm burr is used to create a finishing cutter radius 2380 formed around the eminence. As shown in FIG. 39C, there is a dotted line 2330 in which a 3.2 mm burr is used for machining a keel 2352 and pegs 2354 for a tibial baseplate 2350.

For peg preparation, an interference fit between the bone and the implant is often desired to achieve adequate fixation. With the robot, this level of interference can be customized. The robot will machine away an opening in the bone into which the implant will be impacted, and the diameter of the opening can be tailored to achieve a desired level of interference. For example, a smaller peg hole diameter can be prepared to achieve greater interference between the bone and the implant.

Figure 40:
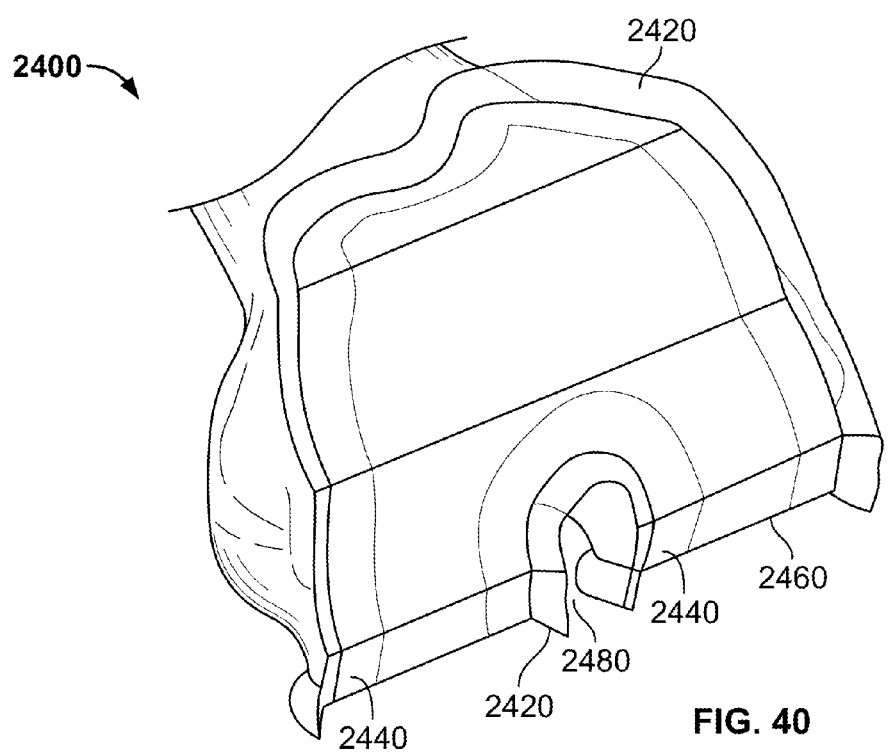
FIGS. 40, 41 and 42 are perspective views of the distal femur after different debulking and finishing procedures are performed.
Figure 41:
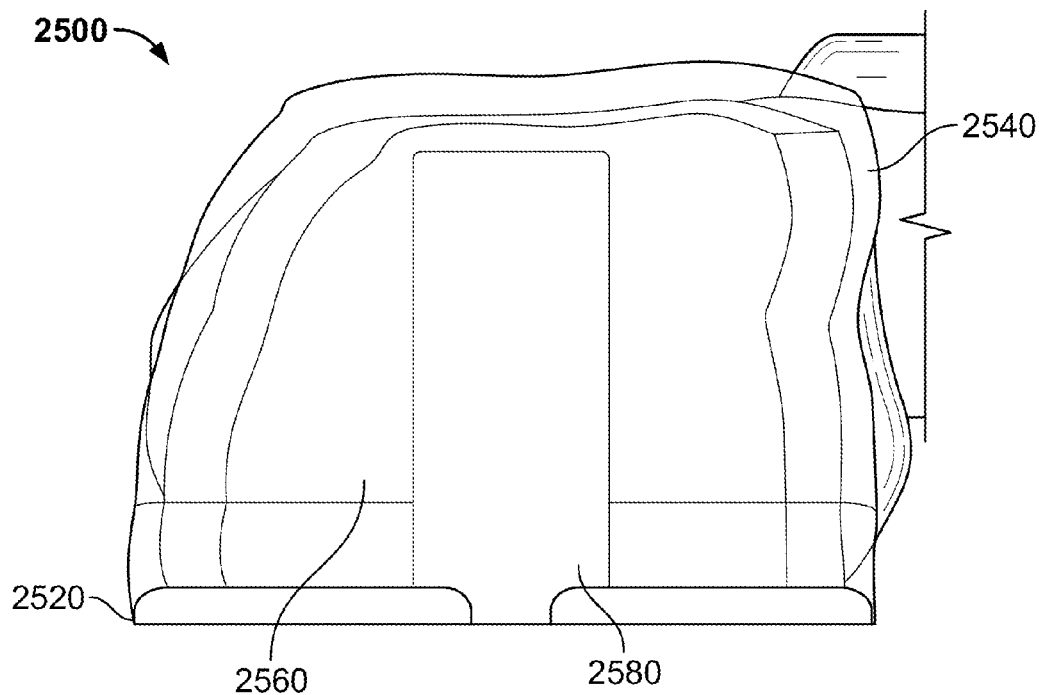
Figure 42:
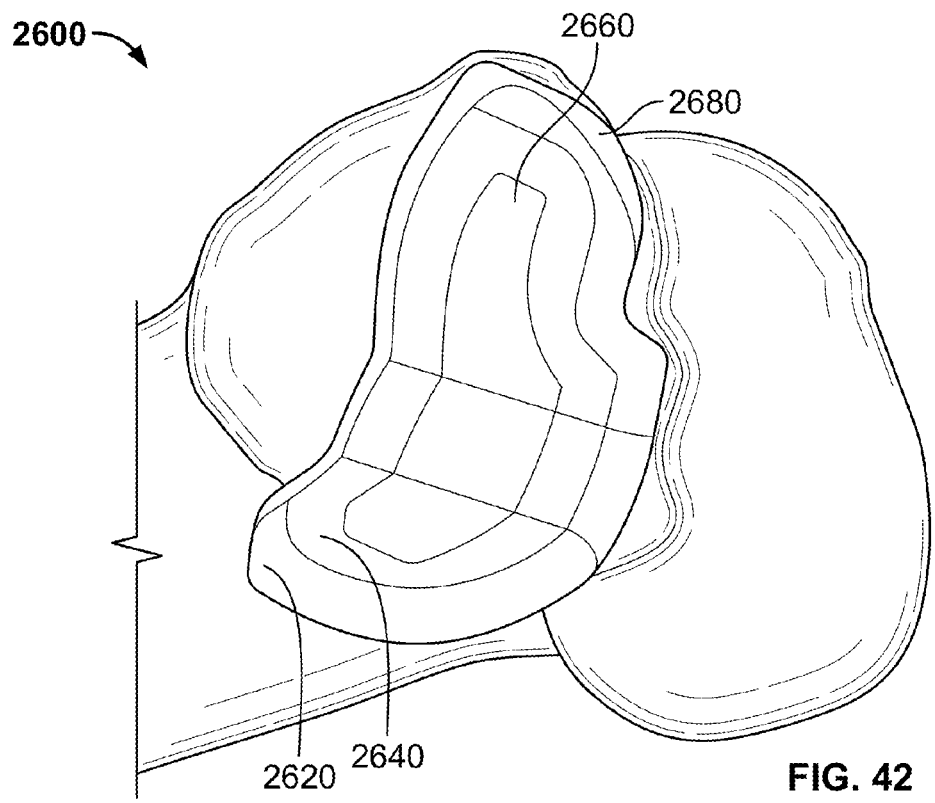
Figure 43A:
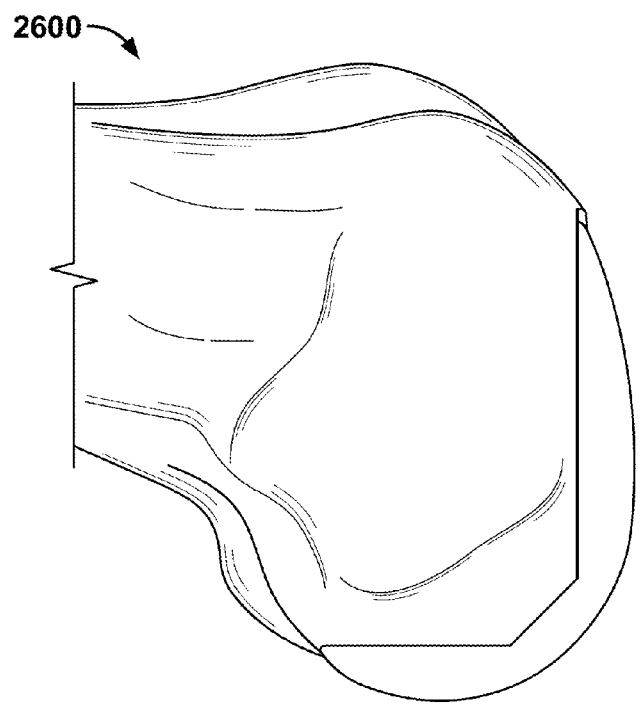
FIG. 43A is a side view and FIG. 43B is a plan view of an unicondylar prosthesis on the partial knee resurfacing region of FIG. 42.
Figure 43B:
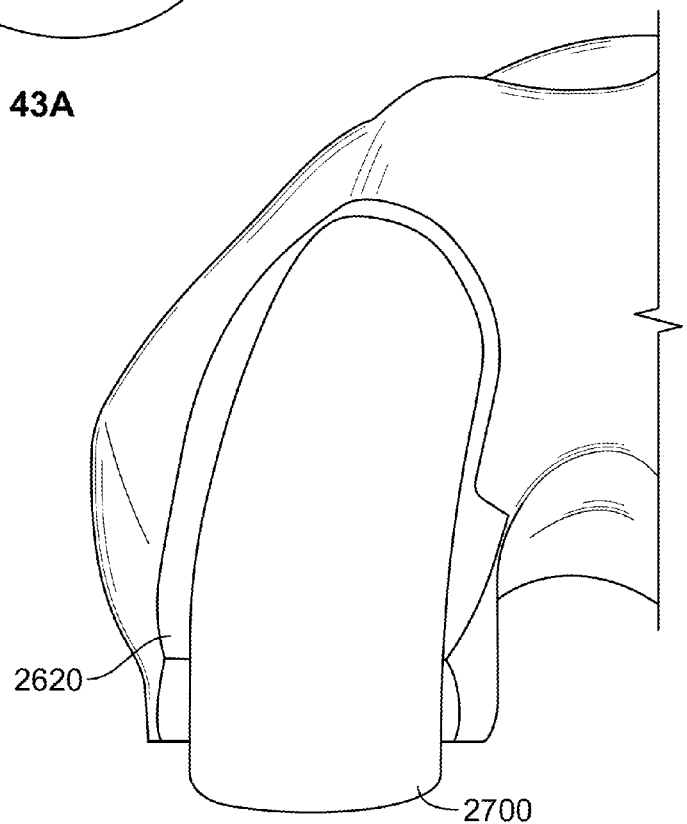

FIGS. 40, 41 and 42 are perspective views of the distal femur after debulking and finishing is performed. As shown in FIG. 40, distal femur 2400 includes an outer tool boundary region 2420, a cortical rim region 2440 and a cancellous bone region 2460. A portion of outer tool boundary region 2420 bounds a cruciate retaining region 2480. As shown in FIG. 41, distal femur 2500 includes an outer tool boundary region 2520, a cortical rim region 2540 and a cancellous bone region 2560. A portion of outer tool boundary region 2520 bounds a posterior stabilization region 2580. As shown in FIG. 42, distal femur 2600 includes a partial knee resurfacing region having an outer tool boundary region 2620, a cortical rim region 2640 and a cancellous bone region 2660. A region 2680 is shown where a finishing cutter is used to minimize the resultant gap between implant and cartilage. FIG. 43A is a side view and FIG. 43B is a plan view of a unicondylar prosthesis 2700 on the partial knee resurfacing region of FIG. 42.

Traditionally, an interference fit is created between the pegs on the implant and the peg preparation in the bone for cementless femoral total knee arthroplasty ("TKA") procedures. Additionally, interference can be created between the implant and the anterior and posterior bone resections. The following embodiments discuss bone preparation methods intended to create additional press-fit between a cementless femoral TKA and the prepared bone. An interference press fit is created between the implant and the bone by preparing the bone with a rib-like pattern on the anterior bone cut surface. The ribs are intended to compact upon impaction of the femoral component. Preferably, the ribs extend along the most anterior bone cut surface, and run distal to posterior, parallel to the intended anterior bone cut surface of the implant.

Figure 44A:
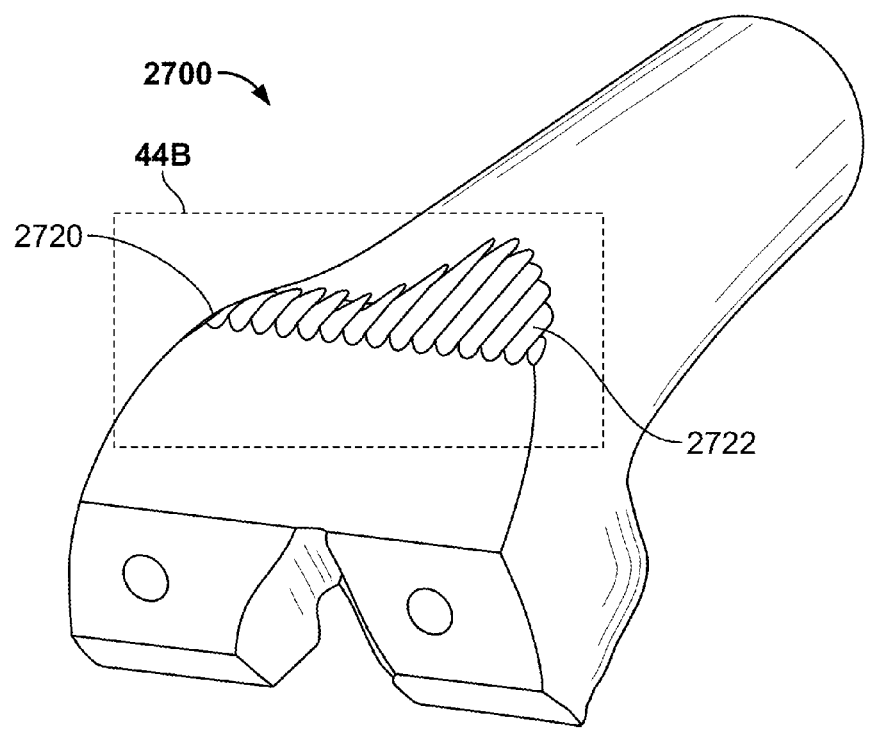
FIG. 44A shows a distal femur including a tolerance profile or ribs extending along an anterior bone cut surface.
Figure 44B:
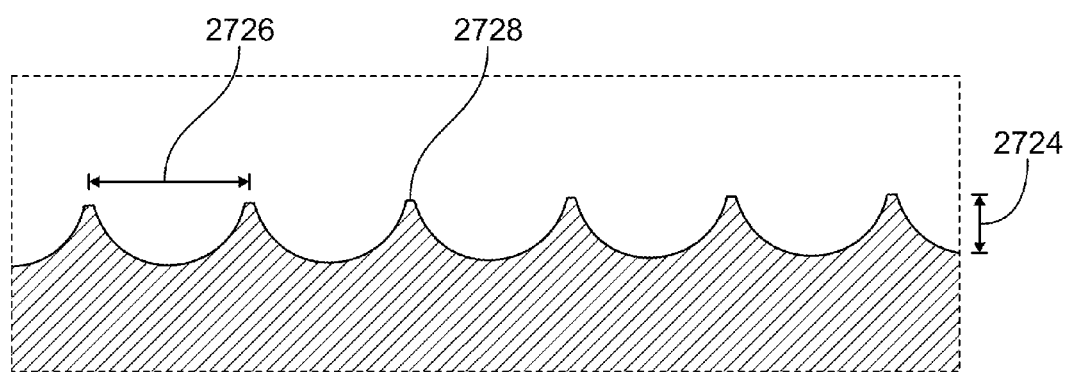
FIG. 44B shows a cross-sectional view of the ribs of FIG. 44A.

As shown in FIG. 44A, distal femur 2700 includes a tolerance profile or ribs 2720 extending along an anterior bone cut surface. When an implant is introduced onto the bone, the ribs 2720 compact and achieve an interference fit between the implant and the bone. FIG. 44B shows a cross-sectional view of ribs 2720 of FIG. 44A. The three-dimensional geometry of ribs 2720 is the result of a rotational cutting tool, such as a burr for example, making a plurality of channeled preparations 2722 into distal femur 2700. In the embodiment shown, the plurality of channeled preparations 2722 follow a substantially linear path. Ribs 2720 have a height 2724, a width 2726 and a plurality of protrusions 2728. Ribs 2720 shown on distal femur 2700 are similar to the tolerance profile 30 shown in FIGS. 3 and 4, for example. In this embodiment, the radius of the finishing burr is preferably 2.5-3.5 mm.

Figure 45:
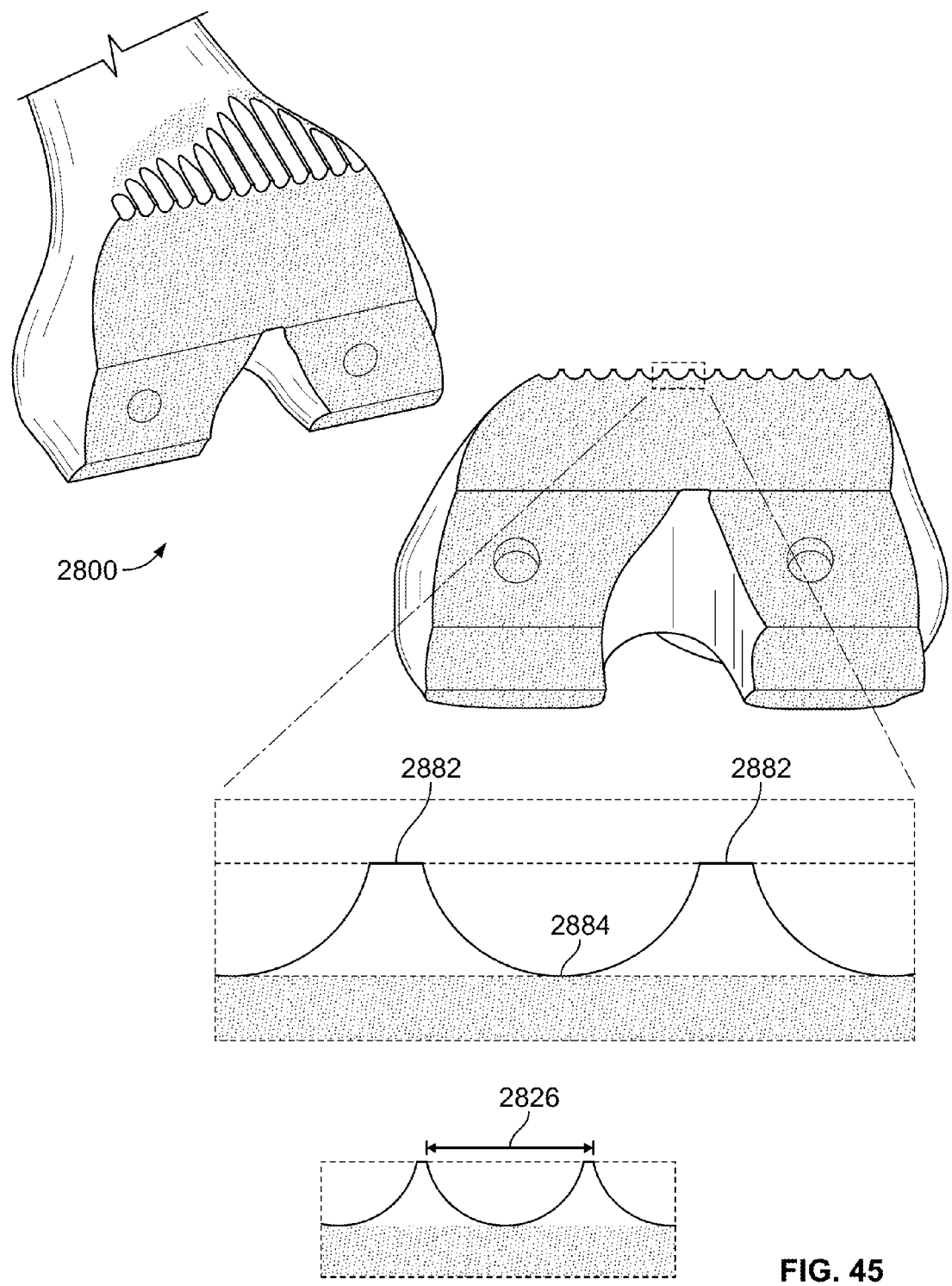
FIG. 45 shows a distal femur with an MMC implant profile.

As shown in FIG. 45, distal femur 2800 includes an MMC implant profile. The peak-to-peak distance between adjacent ribs 2820 can be adjusted to have more or less interference press fit and compaction. Width 2826 of ribs 2820 is defined as the distance from bone peak 2882 to adjacent peak in a transverse direction.

Figure 46:
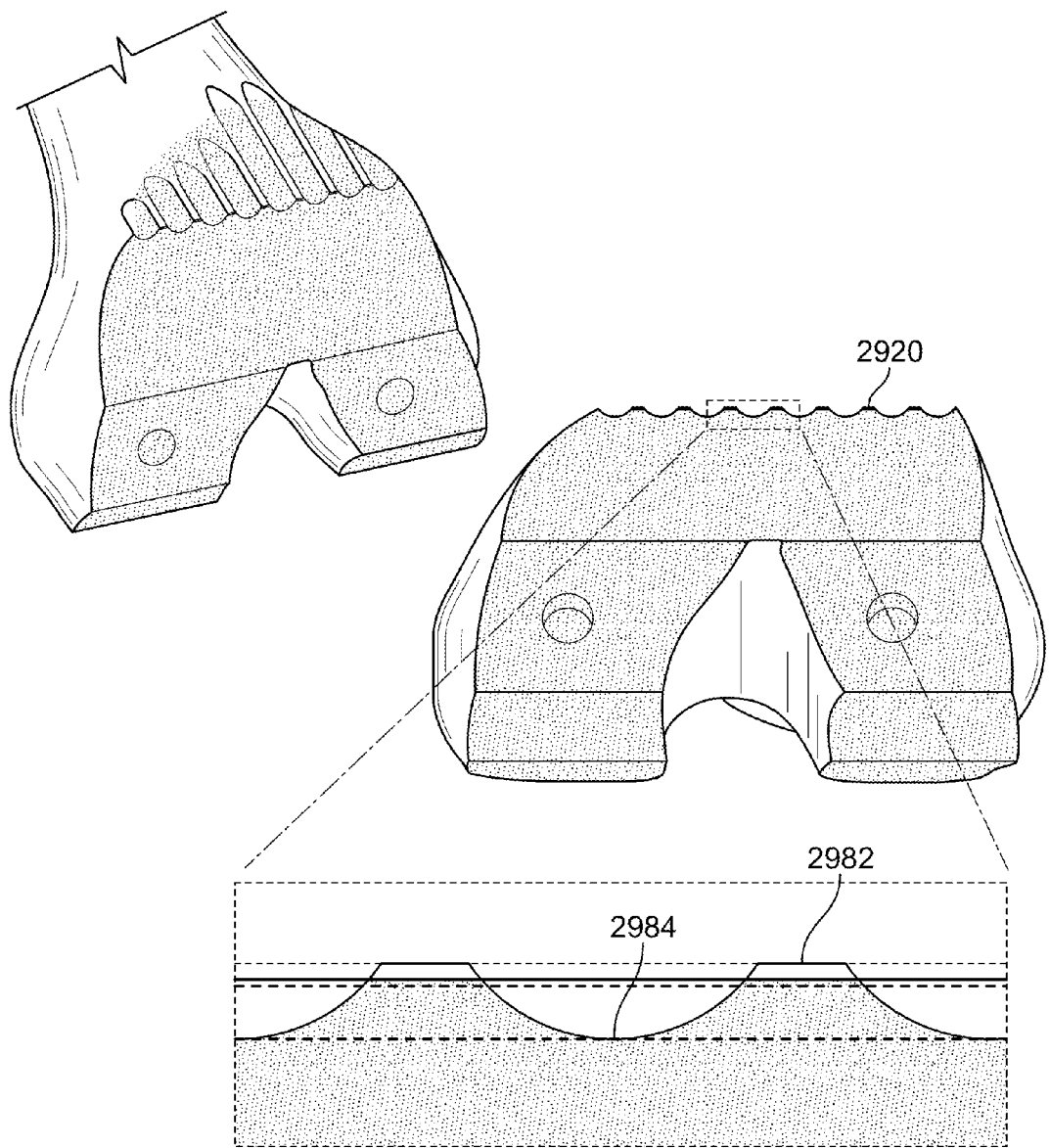
FIG. 46 shows a distal femur with a LMC implant profile.

FIG. 46 shows distal femur 2900 including a LMC implant profile. The bone will be compacted approximately 0.01" upon implantation of the LMC implant. This compaction is shown as the linear distance between a first line adjacent bone peak 2982 and a second line closer to valley 2984.

In other embodiments, this concept of highly toleranced zones of bone preparation may be used for other bone preparation and prosthetic implants throughout the body. Other areas and uses may include bicompartmental knee replacement implants, tricompartmental knee replacement implants, total knee replacement implants, patellofemoral replacement implants, acetabular cup implants, spinal interbody devices, and vertebral body replacements.

The invention claimed is:

1. A method of preparing a bone surface to receive a prosthetic implant thereon, the prosthetic implant having an articular surface and a bone contacting surface, the method comprising:
    resecting the bone surface at a first location to create a first resected region having a first tolerance profile with a first cross-section having peaks and valleys;
    resecting the bone surface at a second location to create a second resected region having a second tolerance profile with a second cross-section less dense than the first cross-section such that the second cross-section has peaks further apart and valleys deeper than the peaks and valleys of the first cross-section; and
    contacting the bone contacting surface of the prosthetic implant with the first resected region.

2. The method of claim 1, further comprising:
    forming at least one recess in the bone surface prior to implanting the prosthetic implant on the bone surface; and
    inserting a retention element extending from the bone contacting surface in the at least one recess in the bone surface.

3. The method of claim 2, including applying downward force to the articular surface of the prosthetic implant to compact bone in the first resected region.

4. The method of claim 1, further comprising:
    resecting the bone surface at a plurality of locations to create a plurality of resected regions each having a tolerance profile with a cross-section, wherein the tolerance profile of each of the plurality of resected regions is denser than the cross-section of the second tolerance profile.

5. The method of claim 4, wherein the tolerance profile of the second resected region is ±0.010 inches and the tolerance profile of the plurality of resected regions is ±0.025 inches.

6. The method of claim 4, wherein a first of the plurality of resected regions is located at an anterior aspect of the bone surface.

7. The method of claim 6, wherein a second of the plurality of resected regions is located at an outer aspect of the bone surface.

8. The method of claim 7, wherein a third of the plurality of resected regions is located at a posterior aspect of the bone surface.

9. The method of claim 8, wherein the cross-section of the tolerance profile of the first of the plurality of resected regions is less dense than the cross-section of the tolerance profile of the second of the plurality of resected regions and is more dense than the cross-section of the tolerance profile of the third of the plurality of resected regions.

10. A method of preparing a bone surface to receive a prosthetic implant thereon, the prosthetic implant having an articular surface and a bone contacting surface, the method comprising:
    resecting the bone surface at an anterior aspect thereof to create a first resected region having a first tolerance profile with a first cross-section having peaks and valleys;
    resecting the bone surface at a posterior aspect thereof to create a second resected region having a second tolerance profile with a second cross-section having peaks further apart and valleys deeper than the peaks and valleys of the first cross-section such that the first cross-section is denser than the second cross-section; and
    contacting the bone contacting surface of the prosthetic implant with the first resected region.

11. The method of claim 10, further comprising:
    forming at least one recess in the bone surface prior to implanting the prosthetic implant on the bone surface; and
    inserting a retention element extending from the bone contacting surface in the at least one recess in the bone surface.

12. The method of claim 11, including applying downward force to the articular surface of the prosthetic implant to compact bone in the first resected region.

13. The method of claim 10, further comprising:
    resecting the bone surface at a plurality of locations to create a plurality of resected regions each having a tolerance profile with a cross-section, wherein the tolerance profile of each of the plurality of resected regions is denser that the cross-section of the second tolerance profile.

14. The method of claim 13, wherein the tolerance profile of the second resected region is ±0.010 inches and the tolerance profile of the plurality of resected regions is ±0.025 inches.

15. A method of preparing a bone surface to receive a prosthetic implant thereon, the prosthetic implant having an articular surface and a bone contacting surface, the method comprising:
    resecting the bone surface at a peripheral region thereof to create a first resected region having a first tolerance profile with a first cross-section having peaks and valleys;
    resecting the bone surface at an anterior region thereof to create a second resected region having a second tolerance profile with a second cross-section having peaks further apart and valleys deeper than the peaks and valleys of the first cross-section such that the first cross-section is denser than the second cross-section; and
    contacting the bone contacting surface of the prosthetic implant with the first resected region.

16. The method of claim 15, further comprising:
    forming at least one recess in the bone surface prior to implanting the prosthetic implant on the bone surface; and
    inserting a retention element extending from the bone contacting surface in the at least one recess in the bone surface.

17. The method of claim 16, including applying downward force to the articular surface of the prosthetic implant to compact bone in the first resected region.

18. The method of claim 15, further comprising:
resecting the bone surface at a plurality of locations to create a plurality of resected regions each having a tolerance profile with a cross-section, wherein the tolerance profile of each of the plurality of resected regions is denser than the cross-section of the second tolerance profile.

19. The method of claim 18, wherein the tolerance profile of the second resected region is ±0.010 inches and the tolerance profile of the plurality of resected regions is ±0.025 inches.

* * * * *